US011464892B2

(12) United States Patent
Lane et al.

(10) Patent No.: US 11,464,892 B2
(45) Date of Patent: Oct. 11, 2022

(54) DEVICES AND METHODS FOR VASCULAR HYPERPERFUSION OF EXTRAVASCULAR SPACE

(71) Applicant: All Vascular Pty Limited, Greenwich (AU)

(72) Inventors: Rodney James Lane, Castlecrag (AU); Matthew James Huckson, Mount Colah (AU); Chris Kyung, West Ryde (AU); David Lane, Double Bay (AU); Nyan Khin, Belmore (AU); Scott Murphy, Kurrajong Heights (AU)

(73) Assignee: All Vascular Pty Limited, Greenwich (AU)

( * ) Notice: Subject to any disclaimer, the term of this patent is extended or adjusted under 35 U.S.C. 154(b) by 507 days.

(21) Appl. No.: 16/335,603

(22) PCT Filed: Mar. 24, 2017

(86) PCT No.: PCT/AU2017/050266
§ 371 (c)(1),
(2) Date: Mar. 21, 2019

(87) PCT Pub. No.: WO2018/053574
PCT Pub. Date: Mar. 29, 2018

(65) Prior Publication Data
US 2020/0038575 A1 Feb. 6, 2020

(30) Foreign Application Priority Data
Sep. 22, 2016 (AU) .................. 2016903834
Sep. 22, 2016 (AU) .................. 2016903836
(Continued)

(51) Int. Cl.
*A61M 1/36* (2006.01)
*A61M 5/145* (2006.01)
(Continued)

(52) U.S. Cl.
CPC ........ *A61M 1/3615* (2014.02); *A61M 1/3613* (2014.02); *A61M 1/3655* (2013.01);
(Continued)

(58) Field of Classification Search
CPC ........ A61M 2025/0063; A61M 1/3655; A61M 1/3659; A61M 1/3661;
(Continued)

(56) References Cited

U.S. PATENT DOCUMENTS 2,547,099 A * 4/1951 Smoot .................. A61M 5/30
604/70
3,585,986 A * 6/1971 Krug .................. A61B 17/3401
604/165.04
(Continued)

FOREIGN PATENT DOCUMENTS

EP 0875262 B1 1/2002
WO 2009136871 A1 11/2009

OTHER PUBLICATIONS

International Search Report in International Patent Application No. PCT/AU2017/050266 dated Aug. 9, 2017.
(Continued)

*Primary Examiner* — Theodore J Stigell
(74) *Attorney, Agent, or Firm* — Greenberg Traurig, LLP; David J. Dykeman; Jaime L. Burke

(57) ABSTRACT

A method of delivering a therapeutic substance for treatment to a region of the body through vascular isolation and manipulation of fluid flux into and from the region of the body including the steps of: restricting vascular inflow to the region of the body; washing out oncotically active plasma proteins from the region of the body by increasing the outward oncotic pressure gradient from the region of the body; inducing ischemia in the region of the body; controlling the pressure and fluid flow of the main blood vessels to
(Continued)

and from the region of the body; providing the therapeutic substance to the region of the body when the fluid flow to the region of the body is controlled.

14 Claims, 38 Drawing Sheets

(30) Foreign Application Priority Data

| Dec. 5, 2016 | (AU) | ................................ | 2016904991 |
| Dec. 8, 2016 | (AU) | ................................ | 2016905067 |
| Dec. 8, 2016 | (AU) | ................................ | 2016905068 |

(51) Int. Cl.
  *A61M 39/02* (2006.01)
  *A61M 39/00* (2006.01)
  *A61M 25/09* (2006.01)
  *A61M 25/10* (2013.01)

(52) U.S. Cl.
  CPC .......... *A61M 5/1452* (2013.01); *A61M 39/00* (2013.01); *A61M 39/0208* (2013.01); *A61M 25/09* (2013.01); *A61M 25/1011* (2013.01); A61M 2025/09008 (2013.01); A61M 2025/105 (2013.01); A61M 2025/1052 (2013.01); A61M 2039/0205 (2013.01); A61M 2210/0693 (2013.01); A61M 2210/1007 (2013.01); A61M 2210/1071 (2013.01)

(58) Field of Classification Search
  CPC .... A61M 2005/31516; A61M 39/0208; A61M 1/3615; A61M 1/3613; A61M 5/1452; A61M 25/02; A61M 25/09; A61M 25/1011; A61M 2025/09008; A61M 2025/1058; A61M 2025/1052; A61M 2039/0205; A61M 39/12; A61M 1/3639; A61M 39/10; A61M 39/00
  USPC ........................................ 604/170.01, 165.04
  See application file for complete search history.

(56) References Cited

U.S. PATENT DOCUMENTS

| 3,853,126 | A | | 12/1974 | Schulte |
| 4,133,312 | A | | 1/1979 | Burd |
| 4,318,401 | A | * | 3/1982 | Zimmerman ...... A61B 17/3415 |
| | | | | 604/165.01 |
| 4,701,159 | A | | 10/1987 | Brown et al. |
| 5,047,021 | A | | 9/1991 | Utterberg |
| 5,195,980 | A | | 3/1993 | Catlin |
| 5,405,324 | A | | 4/1995 | Wiegerinck |
| 5,814,017 | A | * | 9/1998 | Kashmer ............. A61M 5/5013 |
| | | | | 604/110 |
| 6,217,561 | B1 | | 4/2001 | Gibbs |
| 6,221,057 | B1 | | 4/2001 | Schwartz et al. |
| 6,287,273 | B1 | | 9/2001 | Allers et al. |
| 6,592,544 | B1 | | 7/2003 | Mooney et al. |
| 6,699,231 | B1 | | 3/2004 | Sterman et al. |
| 7,766,853 | B2 | | 8/2010 | Lane |
| 7,914,495 | B2 | | 3/2011 | Amor |
| 8,419,672 | B2 | | 4/2013 | Lane |
| 8,652,109 | B2 | | 2/2014 | Guala |
| 9,078,982 | B2 | | 7/2015 | Lane et al. |
| 2004/0167478 | A1 | | 8/2004 | Mooney et al. |
| 2014/0207060 | A1 | | 7/2014 | Hochareon |

OTHER PUBLICATIONS

International Preliminary Report on Patentability in International Patent Application No. PCT/AU2017/050266 dated Jan. 18, 2019.

* cited by examiner

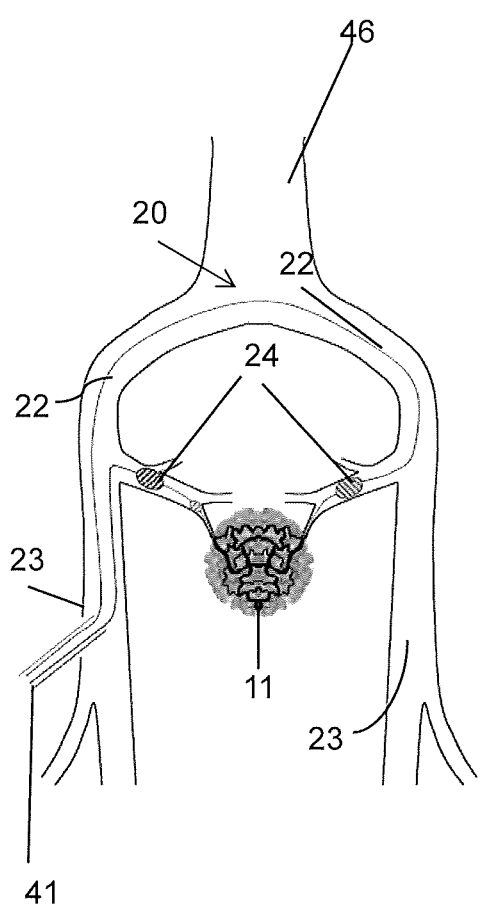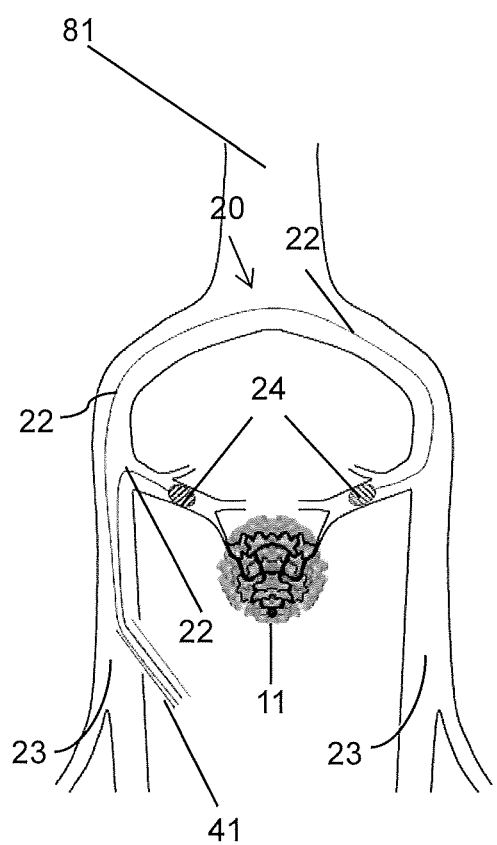
Figure 2
Figure 1

DEVICES AND METHODS FOR VASCULAR HYPERPERFUSION OF EXTRAVASCULAR SPACE

CROSS-REFERENCE AND CLAIM OF PRIORITY TO RELATED APPLICATIONS

This application is a U.S. national phase application of PCT International Patent Application No. PCT/AU2017/050266, filed on Mar. 24, 2017, which claims the benefit of and priority to Australian Application No. 2016903834, filed Sep. 22, 2016, Australian Application No. 2016903836, filed Sep. 22, 2016, Australian Application No. 2016904991, filed Dec. 5, 2016, Australian Application No. 2016905067, filed Dec. 8, 2016 and Australian Application No. 2016905068, filed Dec. 8, 2016, each of which are hereby incorporated by reference in their entireties.

FIELD OF THE INVENTION

The present invention relates to improvements in vascular isolation of organs and segments thereof and, in particular, to improved devices and methods for vascular isolation of human extravascular spaces in organs and segments thereof, so as to enhance delivery and activity of therapeutic agents, such as chemotherapeutic agents and stem cells, to those extravascular spaces. The present invention additionally relates to devices for engaging with vascular spaces and segments thereof.

BACKGROUND OF THE INVENTION

Arterial or venous engagement and access for extended periods is required in many circumstances for a variety of medical therapies and treatments. This typically involves cannulation into an artery or vein. The interface between the vein or artery and cannula requires pressure to deliver materials or receive blood and minimise the ability for blood to stagnate around the interface thereby leading to thrombosis.

When blood is not being taken or substances are not being delivered into the vein or artery the lumen between the cannula and the vein or artery must be plugged to stop blood escaping. Typically, the end of the cannula and/or plug includes edges or protrusions or recesses that extend into the vein or artery or that result in an area of dead space in the cannula. Protrusions and recesses present a formation that potentially allows blood to pool and stagnate giving rise to the conditions where thrombosis can occur. Dead space also gives rise to an area where blood can pool and stagnate also presenting a situation where thrombosis can occur. The dead space may also present an area where gas collects giving rise to the risk of a gas embolism forming.

The access devices used in such treatments or therapies typically comprise a cannula with one end connected to the circulatory system of a patient, and adaptor ports on the other end connected to a blood flow pump or other injection device. When not in use, the isolation system has relied on a plunger that is slidable within the cavity of the cannula to close access to the cavity and so to prevent fluid communication between the circulatory system and any of the ports of the access device. Such access devices may be referred to as single lumen access devices.

U.S. Pat. Nos. 7,766,853 and 8,419,672 describe such access devices for remote access isolation systems. Related access devices and systems are described in U.S. Pat. No. 9,078,982. Each of these three patents, also by the present inventor, are incorporated, in their entirety, herein by reference.

When a venous or arterial access, such as a cannula, is connected to a patient's blood vessel at a perpendicular angle, the tip of a plunger can be slid through the cavity or lumen of the cannula until it reaches the location where the proximal end of the cannula is connected to the wall of the vessel. The plunger can thus, after use of the cannula, completely prevent the filling of the patient's blood into the lumen of the cannula, thereby avoiding fluid stasis which may otherwise cause thrombosis. However, when a cannula is connected to the patient's blood vessel at a non-perpendicular angle, the conventional cylindrical shape of the tip of the plunger is not capable of preventing the filling of a small amount of blood into a lower part (called "the dead space") of the lumen of the cannula unless the tip is slid further through the lumen of the cannula and a leading part of the tip protrudes into the lumen of the vessel. Such a dead space within the lower part of the cannula's lumen or, if the dead space is occupied by the plunger tip, such a protrusion of the leading part of the tip into the vessel's lumen, can be responsible for haemodynamic disturbances, including fluid stasis, within the patient's circulatory system that could result in thrombotic events.

When a single lumen access device of the kind described in these patents, such as a cannula, is connected to a patient's blood vessel at a perpendicular angle, the tip of a plunger can be slid through the cavity or lumen of the cannula until it reaches the location where the proximal end of the cannula is connected to the wall of the vessel. The plunger can thus, after use of the cannula, completely prevent the filling of the patient's blood into the lumen of the cannula, thereby avoiding fluid stasis which may otherwise cause thrombosis. However, when a cannula with an appropriately chamfered proximal end is connected to the patient's blood vessel at a non-perpendicular angle, the conventional cylindrical shape of the tip of the plunger is not capable of preventing the filling of a small amount of blood into a lower part (called "the dead space") of the lumen of the cannula unless the tip is slid further through the lumen of the cannula and a leading part of the tip protrudes into the lumen of the vessel. Such a dead space within the lower part of the cannula's lumen or, if the dead space is occupied by the plunger tip, such a protrusion of the leading part of the tip into the vessel's lumen, can be responsible for haemodynamic disturbances, including fluid stasis, within the patient's circulatory system that could result in thrombotic events.

Furthermore, access devices with multi-access treatment caps are known, as shown in FIG. 51 of U.S. Pat. No. 9,078,982 by the present inventor. However, those access devices with multi-access treatment caps have access ports which are such that only a single catheter may be received through a selected access port and then through the lumen of the access device, and therefore each such device can only facilitate either an outflow from the circulatory system to a blood flow pump or an inflow from a blood flow pump in the circulatory system, but not both. That is, those access devices with multi-access treatment caps cannot facilitate two or more inflow and outflow catheters at any one time because the lumen of those devices is unable to receive two or more catheters. Additionally, those multi-access treatment caps do not enable a catheter to be directed into specific positions with use of the multi-access treatment cap.

Arterial or venous infusions of pharmaceutical or other therapeutic agents are standard practice for chemotherapy in treating neoplasia, for gene therapy, and for stem cell therapy. The effect on the targeted tissue is diminished as a result of the dilution of the therapeutic agent by the normal flow of blood and/or the detoxification of the therapeutic agent by blood. To counter these effects, "stop flow" techniques have been developed, usually by obstructing the inflow and outflow from the targeted tissue.

Standard techniques exist, for example, for the chemotherapeutic treatment of neoplasia in the pelvis, in which the aorta and inferior vena cava are obstructed, tourniquets are applied to the legs and the isolated segment is then infused with a chemotherapeutic agent for a short period of time within the ischemic time of the pelvis. An alternative approach is to remove the blood containing the chemotherapeutic agent and use various extracorporeal filters to neutralize the agent before systemic recirculation. The aim in that situation is to minimise the toxic side effects when the blood containing the chemotherapeutic agent is released into the systemic circulation. This type of approach may be done operatively in the liver by cannulating the portal vein and the hepatic artery of the liver, using pumps to recirculate the agent and using an extracorporeal filter to minimise the systemic effects. This is called "isolated hepatic infusion".

Remote access isolation systems have been described for regional hyperperfusion to increase the blood flow to an intravascular space (see U.S. Pat. No. 9,078,982). Generally, hyperperfusion occurs when an above normal amount of fluid or cells passes through a space. Such isolation systems require an inflow port, an outflow port, an isolation balloon, and a pump to control the blood flow to the targeted organ. The pressures created are up to 4 times the normal arterial mean pressures with an increase of up to 8 times the normal flow. An aim of the hyperperfusion in U.S. Pat. No. 9,078,982 is to remove symptoms of an ischemic limb, in the short term to prevent amputation, and in the longer term to produce an increase in the shear stress to grow new blood vessels.

The inevitable effect of hyperperfusing therapeutic agents regionally to a desired intravascular space is that the agents will then move into the interstitial space from where they can enter not only the target area but also the draining lymphatic channels and lymph nodes. The approach has important ramifications in the treatment of neoplasia, as many malignant cells invade the lymphatic channels, migrate into the lymph nodes, multiply and then embolise via the thoracic duct before they move into the vascular system from where they spread systemically. Lymph nodes that are involved are notoriously difficult to treat because of their small size. Tumour recurrence often arises from residual tumours in lymph nodes and among lymph cells. Other problems relating to treatment of neoplasia arise from malignant cells residing in small numbers in relatively ischemic tissue, such that systemic treatment will have diminished effect. Some tumours are also known to induce a higher interstitial pressure partly due to a surrounding pseudo-capsule related to compression of normal structure and or secondary inflammatory effects. There are also some malignant cells that do not multiply and so those therapeutic agents which mainly affect cell division will have little or no effect on such cells.

The access devices used in such remote access isolation systems for regional hyperperfusion to a target area and for therapies or treatments where arterial or venous engagement for extended periods is required include cannulas, catheters (and especially balloon catheter systems), balloons, plungers, adaptor ports and other devices required for these therapies or treatments.

Remote access isolation systems in the past have been able to provide intermittent or acute access to a patient's circulatory system for the purpose of hyperperfusion to ischemic limbs. The access devices used in such systems typically comprise a cannula with one end connected to the circulatory system of a patient, and adaptor ports on the other end connected to a blood flow pump. When not in use, the isolation system has relied on a plunger that is slidable within the cavity of the cannula to close access to the cavity and so to prevent fluid communication between the circulatory system and any of the ports of the access device. Such access devices may be referred to as single lumen access devices.

U.S. Pat. Nos. 7,766,853 and 8,419,672 describe such access devices for remote access isolation systems. Related access devices and systems are described in U.S. Pat. No. 9,078,982, Each of these three patents, also by the present inventor, are incorporated, in their entirety, herein by reference.

When a single lumen access device of the kind described in these patents, such as a cannula, is connected to a patient's blood vessel at a perpendicular angle, the tip of a plunger can be slid through the cavity or lumen of the cannula until it reaches the location where the proximal end of the cannula is connected to the wall of the vessel. The plunger can thus, after use of the cannula, completely prevent the filling of the patient's blood into the lumen of the cannula, thereby avoiding fluid stasis which may otherwise cause thrombosis. However, when a cannula with an appropriately chamfered proximal end is connected to the patient's blood vessel at a non-perpendicular angle, the conventional cylindrical shape of the tip of the plunger is not capable of preventing the filling of a small amount of blood into a lower part (called "the dead space") of the lumen of the cannula unless the tip is slid further through the lumen of the cannula and a leading part of the tip protrudes into the lumen of the vessel. Such a dead space within the lower part of the cannula's lumen or, if the dead space is occupied by the plunger tip, such a protrusion of the leading part of the tip into the vessel's lumen, can be responsible for haemodynamic disturbances, including fluid stasis, within the patient's circulatory system that could result in thrombotic events.

Furthermore, access devices with mufti-access treatment caps are known, as shown in FIG. 51 of U.S. Pat. No. 9,078,982 by the present inventor. However, those access devices with multi-access treatment caps have access ports which are such that only a single catheter may be received through a selected access port and then through the lumen of the access device, and therefore each such device can only facilitate either an outflow from the circulatory system to a blood flow pump or an inflow from a blood flow pump in the circulatory system, but not both. That is, those access devices with multi-access treatment caps cannot facilitate two or more inflow and outflow catheters at any one time because the lumen of those devices is unable to receive two or more catheters.

It has been found by the present inventor that there are several ways in which vascular isolation can enhance delivery of therapeutic agents to human organs and seaments thereof, such as tumours, and thereby enhance therapeutic activity.

Firstly, an enhancing mass effect can be produced by the delivery of the agent to a specifically isolated target area to increase the concentration of the agent in a confined mass of tissue in that area. This effect is based on relative tumour mass, and is called "mass targeting". The degree of enhancement depends upon the mass of the targeted tissue compared to the total mass of the body. For example, a pancreatic head cancer typically may weigh 35 g on clinical presentation. In a 70 kg man, the therapeutic advantage of mass targeting approximates 2000× that of systemic intravenous delivery.

A second enhancing effect of vascular isolation is called "exposure time prolongation" and involves the avoidance of washout or dilution of the agent by controlling the inflow and outflow for a period of time specifically within the ischemic time of the relevant organ. This is a time effect which multiplies the first mentioned mass effect. In pharmacokinetic language this is known as the "area under the curve", which is derived from a graph where agent concentration is plotted against time.

A third enhancing effect of vascular isolation is the capacity to neutralize the agent, such as by administering an antidote before the isolation is reversed. This is called "neutralization of residual active chemotherapy". In order to avoid any systemic effects, it is possible to reverse the flow through the isolated organ or segment thereof and extract the residual agent and discard it before it has left the organ. This is called the residual concentration of the agent and can be measured by assessing the concentration of agent in the discarded volume.

A fourth enhancing effect of vascular isolation is by control of the osmolar pressure gradient into the isolated target area, consequently controlling he oncotic pressure. Although access devices allow for control of the arterial inflow and venous outflow, even more targeted therapy may result from substitution of the intravascular plasma proteins with hypo-osmolar solutions containing the therapeutic agents. A hypo-osmolar solution creates an osmolar pressure gradient which controls movement of the therapeutic agents from the intravascular space to the extravascular space, and especially to the interstitial space surrounding the tumour cells. The interstitial space contains the metabolic substrates required by the tumour cells, and is drained by the lymphatic system. So, not only can tumour cells be specifically targeted in this way, but the lymphatic channels and lymph nodes draining from the tumour cells can also be targeted.

The control of the osmolar pressure gradient can include controlling the oncotic pressure. The control of oncotic pressure enables the removal or partial removal of the intravascular protein.

A further way in which vascular isolation can enhance therapeutic activity is to selectively control the venous outflow of an organ, whilst simultaneously controlling the arterial inflow.

Again, with respect to the present invention, yet still a further way in which vascular isolation can enhance therapeutic activity is to increase the venous outflow pressure above the typical mean arterial pressure (MAP) and mean capillary pressure (MCP) as much as possible allowing an increased hydraulic force for injection up to and including the vascular pressure so that this hydraulic force can be directed laterally. This can be measured with instruments attached to the infusion system.

In the past there have been a variety of external fistulae usually for haemodialysis procedures. The original shunts were described by Quentin Scribner, Allen Brown and Thomas Shunts. There may be direct anastomoses to the donor input artery and to the receiving vein (Thomas and Allen Brown). In some cases endoluminal connections were used without anastomosis and with the ligation of the distal vessels (Quentin Scribner). To access the systemic circulation the arterio and venous sides were temporarily clamped and the interconnecting device removed. This device was commonly a simple endoluminal connecting tube with a possibility of easy disconnection. There are clear safety issues. This system was being connected to the therapeutic or diagnostic system. The prime example is renal haemodialysis.

Where external fistulae have been used high flow rates are common. The high flow rates can contribute to congestive cardiac failure due to the high flow rates that manifests itself as peripheral oedema, lethargy, shortness of breath and chest pain. It can also cause peripheral "Steal" syndrome where the high flow rate causes ischemia in the regions distal the fistula. High flow can also cause venous hypertension.

SUMMARY OF INVENTION

In a first embodiment, the present invention seeks to provide a method of delivering a therapeutic substance for treatment to a region of the body through vascular isolation and manipulation of fluid flux into and from the region of the body including the steps of: restricting vascular inflow to the region of the body; washing out oncotically active plasma proteins from the region of the body by increasing the outward oncotic pressure gradient from the region of the body; inducing ischemia in the region of the body; controlling the pressure and fluid flow of the main blood vessels to and from the region of the body; providing the therapeutic substance to the region of the body when the fluid flow to the region of the body is controlled.

In controlling the pressure and fluid flow of the main blood vessels to wash out proteins and enable therapeutic treatment, the present invention seeks to avoid the need for drug usage to expel albumens and allow therapeutic substances to cross extravascular space barriers.

Preferably, the region of the body is an organ.

Preferably, pressure through the vascular inflow is controlled to be less than or equal to 20 mmHg.

Preferably, the pressure through the vascular inflow is controlled to induce critical capillary closure.

Preferably, the oncotically active plasma proteins are washed out at between 28 mm Hg to 35 mm Hg.

Preferably, outflow of the therapeutic substance from the region of the body is occluded using positive end expiratory pressure (PEEP).

By using PEEP, the need for mechanical occlusion of outflow ports to restrict the escape of therapeutic substances through the outflow is avoided.

Preferably, outflow of the therapeutic substance from the region of the body is controlled using relative movement of limbs of the body.

Preferably, the therapeutic substance is hyperperfused into the region of the body.

Hyperperfusion avoids the use of drugs to assist with substance transfer into extravascular spaces.

Preferably, the hyperperfusion is provided at less than or equal to 35 mm Hg.

Preferably, the occlusion of vascular flow is achieved with multi balloon catheter line insertion to at least one of the blood vessels surrounding the target area.

Preferably, the therapeutic treatment includes at least one of chemotherapy, supply of nanoparticles, stem cells, immunotherapy and or gene therapy.

Preferably, the manipulation of fluid flux includes at least one of occlusion of flow, partial occlusion of flow, isoperfusion or hyperperfusion of the main axial vessels to the target area.

Preferably, the manipulation of fluid flux is achieved with at least one of endovascular or extravascular devices.

Preferably, the method includes assessing and modulation of the fluid pressure of fluid within the blood vessels according to infusion.

Preferably, the method includes the steps of: delivering the therapeutic treatment to an interstitial space where tumour cells reside, or to the necrotic centers of tumours along an oncotic gradient penetrating pseudocapsule following an oncotic gradient; providing fluid that traverses the lymphatics and delivers treatment to lymph nodes; and repeating delivery of therapeutic treatment over time may target cells that are not dividing at one particular treatment cycle.

By using the oncotic gradient to target tumour cells, the cells can be better targeted without collateral damage.

In a second embodiment, the present invention seeks to provide an assembly for delivering a therapeutic treatment to a region of the body through vascular isolation and manipulation of fluid flux into and from the region of the body including: a first occlusion device adapted to restrict vascular inflow to the region of the body; a second occlusion arrangement to restrict vascular outflow from the region of the body; wherein the first occlusion device is adapted to increase the outward oncotic pressure gradient from the region of the body to wash out oncotically active plasma proteins from the region of the body so as to leave the region of the body in a state of ischemia; an injection device arranged to provide a therapeutic substance for the therapeutic treatment when the region is in ischemia; and a removal device arranged to remove the therapeutic substance from the region of the body.

Preferably, the region of the body is an organ.

Preferably, the first occlusion device is arranged to control pressure through the vascular inflow to be less than or equal to 20 mm Hg.

Preferably, the pressure through the vascular inflow is controlled to induce critical capillary closure.

Preferably, the oncotically active plasma proteins are washed out at between 28 mm Hg to 35 mm Hg.

Preferably, outflow of the therapeutic substance from the region of the body is occluded using positive end expiratory pressure.

Preferably, outflow of the therapeutic substance from the region of the body is controlled using relative movement of limbs of the body.

Preferably, the therapeutic substance is adapted to be hyperperfused into the region of the body through a catheter.

Preferably, the hyperperfusion is provided at a pressure below the venous outflow pressure from the region of the body.

Preferably, the hyperperfusion is provided at less than or equal to 35 mm Hg.

In a third embodiment, the present invention seeks to provide a vascular access device for prolonged use including: a chamfered cannula including a chamfered cannula end arranged to engage with a blood vessel at an angle; and a removable plunger arranged to block and seal a lumen of the cannula; wherein the removable plunger includes a chamfered end arranged to eliminate dead space within the cannula when the plunger is fully inserted in the cannula to block the lumen of the cannula.

The elimination of deadspace minimises the risk of thrombosis.

Preferably, the chamfered end of the removable plunger is arranged so that it does not protrude into the blood vessel when the plunger is fully inserted into the cannula to block the cannula.

Preferably, the chamfered cannula end and the chamfered end of the plunger have the same chamfered angle.

Preferably, the cannula includes an inner wall profiled to mateably correspond to outer stem wall of the plunger.

Preferably, the inner wall of the cannula is profiled so that the plunger cannot rotate due to the mateable correspondence with the outer stem wall of the plunger. The vascular access device as claimed in Claim 33 or Claim 34, wherein projections of the outer stem wall of the plunger are arranged to be received in recesses in the inner wall of the cannula.

Preferably, the mating correspondence of the cannula inner wall and the plunger outer wall are arranged so that the chamfered cannula end is parallel with and aligned with the chamfered end of the plunger when the plunger is fully inserted in the cannula.

Preferably, the cannula includes a graft end arranged to engage with a blood vessel and a body portion, wherein the graft end is arranged to connect with the body portion.

Preferably, the cannula includes a connector assembly distal to the graft end arranged to connect to a medical supply device.

Preferably, the connector assembly is arranged to connect with the body portion.

In a fourth embodiment, the present invention seeks to provide, a multiport adaptor for a cannula system including: a plurality of tubes feeding into a central lumen; wherein the central lumen is arranged to connect to a main cannula line that is arranged to connect to the vasculature.

Preferably, the plurality of tubes can be used to provide a plurality of cannulas into the vasculature via the central lumen.

Preferably, the plurality of cannulas is used to create an anastomosis in the vasculature.

Preferably, each of the plurality of tubes is arranged to receive and feed a guide wire into the central lumen.

Preferably, the plurality of tubes are flexible and arranged so that the lumens in each of the tubes do not intersect.

Preferably, the guide wires are arranged to be fed into the vasculature individually or together.

Preferably, the guide wires are arranged to include balloons.

Preferably, the guide wires are arranged to be directed to inflow and outflow vasculature bodies of a particular region so that the particular region can be isolated with medical devices associated with the guide wires.

Preferably, each of the plurality of tubes is arranged to connect an external medical device.

Preferably, the plurality of tubes are arranged to connect to the external medical device with a luer lock.

Preferably, the plurality of tubes are arranged to provide a plurality of endovascular devices into the vasculature simultaneously.

In a fifth embodiment, the present invention seeks to provide an external arterio-venous fistula connection arranged to connect between an arterial cannula and a venous cannula including an arterial connection means arranged to sealingly connect to the arterial cannula, a venous connection means arranged to sealingly connect to the venous cannula to create a sealed passageway and at least one reusable access portal; wherein the access portal is arranged to receive a catheter for insertion into the vein connected to the venous cannula or artery connected to the arterial cannula.

Preferably, the external arterio-venous fistula connection includes a reusable arterial access portal arranged to receive a catheter for insertion into the arterial cannula and a venous access portal arranged to receive a catheter for insertion into the venous cannula.

In a sixth embodiment, the present invention seeks to provide an system for increasing hepatic artery flow by using a system of multiple trans-arterial balloons to decrease total intestinal flow therefore decreasing portal flow and activating a hepatic artery buffer response.

BRIEF DESCRIPTION OF THE DRAWINGS

Notwithstanding any other embodiments that may fall within the scope of the present invention, an embodiment of the present invention will now be described, by way of example only, with reference to the accompanying figures, in which:

FIG. 1 is a schematic representation of an arterial occlusion balloon positioning arrangement for control of arterial flow in the pelvis region according to an embodiment of the present invention;

FIG. 2 is a schematic representation of a vascular occlusion balloon positioning arrangement for control of vascular flow according to an embodiment of the present invention;

DETAILED DESCRIPTION OF THE INVENTION

Figure 3:
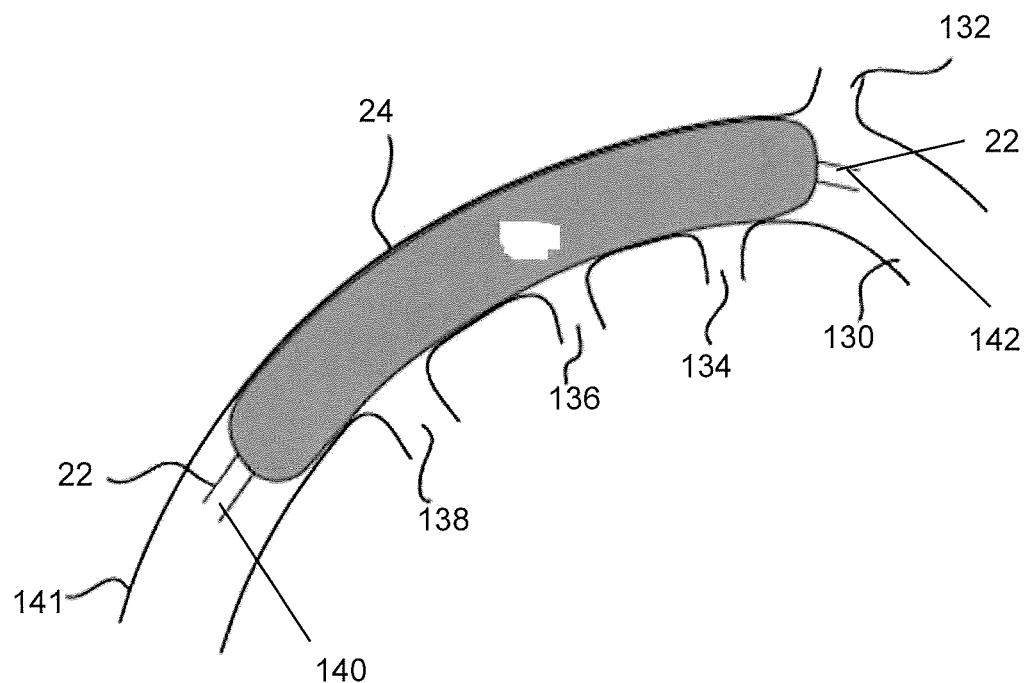
FIG. 3 is a schematic representation of a vascular occlusion balloon positioning arrangement of a single balloon catheter system which provides control of collateral vascular blood flow for use in vascular isolation of the right breast according to an embodiment of the present invention.

Broadly, with reference to FIGS. 1 to 13 an embodiment of the present invention relates to a system and devices for improving the delivery of therapeutic substances for therapeutic treatment into the extra vascular, i.e. interstitial space, where the targeted cells or lesions are situated, specifically hyperperfusing the ischemic interstitial space. Hyperperfusion is defined as to cause an above normal amount of fluid (or cells) to pass through a space. The inevitable effect of hyperperfusing therapeutic agents into the interstitial space is to hyperperfuse the target as well as the draining lymphatic channels and lymph nodes. The concept has important ramifications in the treatment of neoplasia as many of the malignant cells invade lymphatics, migrate into the lymphatic nodes, multiply, then embolise via the thoracic duct and then into the venous system and hence is spread systemically. Lymph node involvement is notoriously difficult to treat related to the small size of lymph nodes. Tumour recurrence often relates to residual tumour in lymph nodes and lymph cells. Other problems relating to treatment of neoplasia relate to malignant cells residing in small numbers in relatively ischemic tissue so that systemic treatment has grossly diminished penetration capacity and hence effect. Some tumours are also known to have a higher interstitial pressure induced partly due to a surrounding pseudocapsule related to compression of normal structure and or secondary inflammatory effects. There are also some malignant cells that are not multiplying and as many therapeutic agents have its main effect on cell division. The physiological laws governing fluid fluxes across capillary membrane is described in Starlings equation.

The Starling equation reads as follows:

$$J_v = K_f([P_c - P_i] - \sigma[\pi_c - \pi_i])$$

where:

$J_v$ is the net trans vascular fluid flow in cubic centimetres per second;

$[P_c - P_i] - \sigma[\pi_c - \pi_i]$ is the net driving force;

$P_c$ is the capillary hydrostatic pressure;

$P_i$ is the interstitial tissue hydrostatic pressure;

$\pi_c$ is the capillary colloid oncotic pressure;

$\pi_i$ is the interstitial tissue colloid oncotic pressure;

$K_f$ is the capillary filtration coefficient—a proportionality constant; and $\sigma$ is the capillary protein reflection coefficient.

The reflection co-efficient is a correction co-efficient that reflects the variability of the oncotic pressure gradient. Typically the reflection co-efficient is less than 1.

Following are approximated values for the variables in the equation for both arterioles and venules in the body:

| Location | $P_c$ (mmHg) | $P_i$ (mmHg) | $\sigma\pi_c$ (mmHg) | $\sigma\pi_i$ (mmHg) |
|---|---|---|---|---|
| arteriolar end of capillary | +35 | −2 | +28 | +0.1 |
| venular end of capillary | +15 | −2 | +28 | +3 |

Assuming that the net driving force declines linearly, then there is a mean net driving force outwards from the capillary as a whole, which also results in more fluid exiting a capillary than re-entering it. The lymphatic system drains this excess.

Changes in the Variables with Hyperperfusion of the Interstitial Space

The following embodiments of the present devices and methods reduce the capillary pressure below the "critical closing pressure". When infusion begins the capillaries reopen and receive the infused substrate. They close again when the infusion is stopped minimising dilution by red cells and plasma. Typically, the critical closing pressure is 20 mm Hg.

Embodiments of the present invention allowing improved pressure driven washout and hyperperfusion of the interstitial space affects the following variables:

(a) Reduction of the Pc as the pressure gradient from the arteriolar to the venules is normally high and the venous capacitance is several times the arteriolar capacitance; reduction of the perfusion pressure is essential to avoid rapid washout of the therapeutic substance.

(b) Increase the oncotic gradient to drive wash out of red blood cells, plasma and protein from the interstitial space.

(c) Elevation of the therapeutic perfusion pressure (Pp) by the infusion catheter. Often the Pp is greater than the original Pc and optimally the Pp is greater than the Pc so that maximum therapeutic agent traverses the basement membrane into the interstitial space.

(d) Reduction of $\pi_c$ as intravascular albumen is important for the oncotic gradient diluting this with saline causes a net outward flux from the intravascular to the extravascular space. This is augmented by the lower molecular weight of many therapeutic agents which passively cross from the intravascular to the extravascular space and therefore aid therapy. Many active therapeutic agents are bound by albumen decreasing their efficiency. For example Oxalyplatin is 70% rapidly and irreversibly bound to Albumen. The described devices are capable of diluting the albumen with the reduction of the oncotic pressure and therefore improving interstitial hyperperfusion.

(e) The devices also allow increasing the filtration coefficient (Kf) by inducing ischemia. Decreased red blood cells intravascular leads to a decrease in oxygen delivery to the capillary endothelium resulting in increased capillary permeability and net increased outward flux. The local ischemia induced vaso dilatation which increases local cross sectional area and therefore increases total outward flux and facilitates extra vascular flow.

Embodiments of the devices of the present invention, at least in part, seek to:
1. reduce, equalise or reverse the Pc, Pv gradient;
2. increase the outward oncotic gradient by diluting or removing intravascular albumen and plasma proteins;
3. optimise therapeutic activity by minimising covalent binding;
4. creating ischemia increasing outward flux across endothelial membranes;
5. increasing the cross sectional area by vaso dilatation induced by ischemia;
6. induce critical closing of capillaries;
7. increase the venous outflow pressure as much as possible; and
8. infuse therapeutic agent up to but not exceeding the key little v so there is no escape of therapy into the systemic circulation.

On the venous side, the devices allow varying degrees of obstruction and depending on the treatment site can be endovascular balloons occluding outflow, positive end expiratory pressure (PEEP) or extravascular in a occlusion device which can transcutaneously be inflated or deflated to control outward flow.

The effects of controlling the intravascular to extravascular flux:
(a) Deliver therapeutic agents to interstitial space where tumour cells reside in small numbers; or to the necrotic centers of tumours along an oncotic gradient.
(b) Have increased capacity to penetrate pseudocapsule following an oncotic gradient.
(c) The fluid traverses the lymphatics and delivers treatment to lymph nodes.
(d) Repeat delivery of agents over time may target cells that are not dividing at one particular treatment cycle.

The critical closing pressure can be used as a valve; normally at 20 mmHg. With an inflow port to an extravascular space occluded the critical closing pressure can be relied on to operate as a valve. After washout of the extra vascular space has occurred and the delivery of the therapeutic agent is complete the capillary system remains closed, then minimal dilution of the area by normal blood can be expected. The pressure difference between hyperperfusion and the intravascular and extravascular space are extreme. The intravascular hyperperfusion requires greater than normally produced pressures by the heart. There is associated with dilatation of the distal vessels increased sheer stress and decreased venous flow. The Gaseous flux from red cells to and from the cells is immediate, i.e. extremely small diffusion time and independent of osmotic pressure and plasma.

In many tumours, the vascular inflow is tortuous, of irregular diameter and may end blindly. There is a reduced flow, pressure and higher resistance which results in reduced chemotherapy delivery. The capillary inflow pressure can drop to 5 mmHg. In these circumstances, hyperperfusion leads to a greater net inflow pressure and increase to the MAP and MCP thereby creating a greater net inflow pressure and greater therapeutic substance delivery. Hyperperfusion also applies to the lymphatic system, creating greater increase in lymphatic flow related to high interstitial pressures. The increase flow containing therapeutic substances is delivered to both lymphatic vessels and nodes.

Possible treatment involving the vascular isolation of organs or anatomical regions of the human body includes but is not limited to the liver, pancreas, pelvic organs, lower limbs, cranial region etc. In various embodiments of the present invention, multiple cannulation systems employing balloons 24 and catheters 22 are inserted into the patient's vasculature using cannulation techniques and subsequently positioned in the arteries and/or veins supplying blood to the target area. The balloons of these balloon catheter systems are then inflated, cutting off or occluding the arterial or venous inflow to the target area and establishing an isolated zone of significantly reduced blood inflow. This isolated zone allows for infusion of therapeutic agents into the target area whilst minimizing systemic exposure. Vascular isolation may be further enhanced by using a separate access device to locate additional balloon catheter systems in the veins so as to occlude venous outflow from the target area or lesion, or by using positive end expiratory pressure (PEEP).

With the isolation zone established, it is within the scope of the present invention to provide infusion to the target area with the flow of blood within the blood vessel or against the flow of blood.

Broadly, the present invention provides a blood vessel occlusion balloon positioning assembly 20 for isolating a region within the body. The blood vessel occlusion balloon positioning arrangement includes an access device 41 arranged to engage, pierce and provide access into a blood vessel, a plurality of catheter lines 22 and catheter balloons 24 located around the catheter lines 22 that are arranged to be inflated within a blood vessel to control the flow of blood. The catheter lines 22 and balloons 24 are arranged around the region within the body to isolate it from blood flow.

Embodiments of the present invention envisage measuring the pressure within blood vessels 23 and controlling the flow and pressure in sections of the blood vessel 23.

FIG. 1 illustrates a blood vessel occlusion balloon positioning arrangement 20 according to an embodiment of the present invention used in the pelvis area from the aorta 81. This can include, but is not limited to, targeting bladder, recto sigmoid, prostate, anal canal, vagina, cervix, uterus, ovary, lymphoma cytoma and sacral tumours. Typically this region includes a number of blood vessels 23. In the arrangement of FIG. 1, the balloon positioning arrangement 20 includes an access device 41 for piercing and providing access to the blood vessels 23, a plurality of catheter lines 22 and catheter balloons 24 around the catheter lines 22 that are arranged to be inflated within a blood vessel to control the flow of blood to a target site. In the embodiment of FIG. 1 the target site is a tumour 11. The catheter lines 22 and balloons 24 are inserted into blood vessels via access device 41 and arranged in blood vessels 23 around the tumour 11 to isolate it from blood flow.

Typically, the targeted organ/region in the pelvis area has a bilateral blood supply requiring control of the blood flow through both supplying blood vessels. This may require a co-rail system with two catheter lines 22 with separate balloons 24. This allows the two catheter lines 22 to place balloons 24 in both blood supply vessels. For example, when the tumour 11 is prostatic carcinoma, a balloon at the origin of the internal iliac system including both the anterior and posterior divisions with a super selective catheter going into the inferior vesical artery which is the desired optimal artery to infuse is used.

FIG. 2 illustrates the use of the balloon positioning arrangement 20 according to an embodiment of the present invention used in blood vessels 23 from the inferior vena cava 46. The blood vessel occlusion balloon positioning arrangement 20 includes an access device 41 for piercing and providing access to the blood vessels 23, a plurality of catheter lines 22 and catheter balloons 24 around the catheter lines 22 that are arranged to be inflated within a vein to control the flow of blood to a target site. In the embodiment of FIG. 2 the target site is a tumour 11. The catheter lines 22 and balloons 24 are arranged in blood vessels 23 around the tumour 11 within the body to isolate it from blood flow.

With respect to FIGS. 1 and 2, where bilateral infusions are required access device 41 can be used from the contralateral side or ipsilateral individually.

FIG. 3 shows an example of a blood flow control balloon 24 to minimise collateral venous flow and optimise infusion of chemotherapeutic agents in the right breast.

Figure 4:
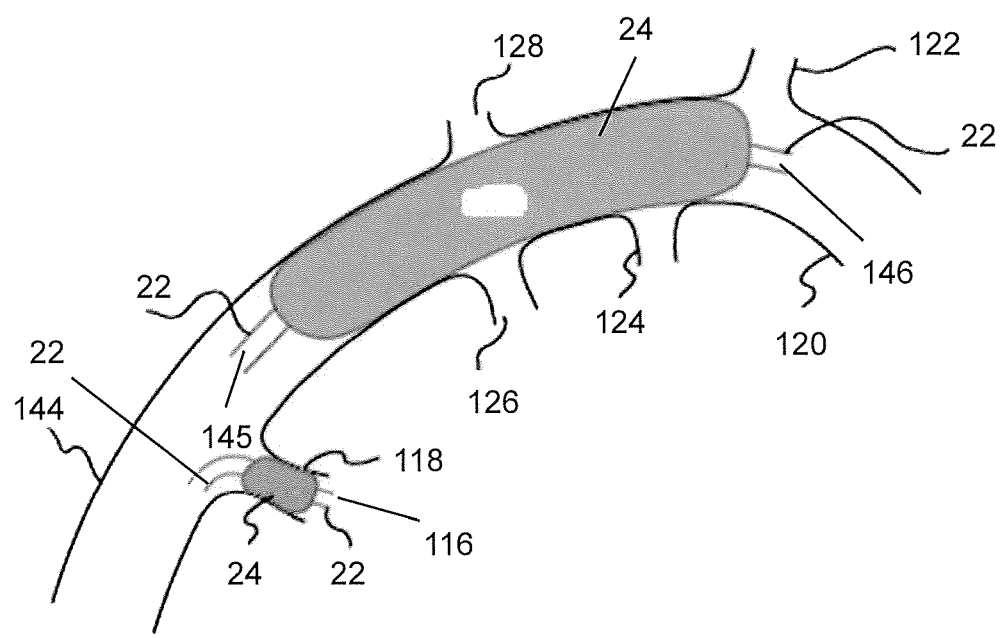
FIG. 4 is a schematic representation of an arterial occlusion balloon positioning arrangement of a multi balloon catheter system which provides control of collateral arterial blood flow for use in vascular isolation of the right breast according to an embodiment of the present invention with super selection of arterial inflow.

FIG. 4 shows an example of a plurality of blood flow balloons 24 being used to minimize collateral arterial flow and further optimise infusion of chemotherapeutic agents in the right breast.

The balloons 24 co-operate to allow selective arterial infusion of chemotherapeutic or other therapeutic agents into a target area via an infusion channel 116 through catheter 22 and balloon 24 in the lateral thoracic artery 118. Collateral blood flow control balloon 114 minimizes arterial collateral flow to the target area by obstruction of the vessels distal to innominate artery 120, the internal thoracic artery 124, the superior thoracic artery 126 and the thyrocervical trunk 128. The common carotid artery 122 feeds into the innominate artery 120.

In one embodiment of the present invention irradiated particles can be injected to the region of the body to be isolated in the above description at the time of arterial infusion or at a later time. The region of the body can have some blood flow to the region at the time the irradiated particles are injected.

With specific reference to FIG. 3, collateral blood flow control balloon 24 minimizes venous collateral flow from the target area by obstruction of vessels proximal the innominate vein 130, the internal thoracic vein 134, the pectoral vein 136 and the lateral thoracic vein 138. In this way, there is obstruction of the axillary and subclavian arterial system to the right breast (as shown in FIG. 4), and there is obstruction of the axillary and subclavian venous system from the right breast (as shown in FIG. 3). The internal jugular vein 132 joins into the right subclavian vein 141. The obstruction of the main venous outflow from the right breast increases the venous pressure in the target area, thereby optimizing the effect of the chemotherapeutic agents on the lesion.

FIG. 3 also shows a shaft 140 that containing separate guidewire and inflation channels (not shown) leading to the balloon 24 via the basilic vein and then the right subclavian vein 141, and an end 142 of the shaft 140.

FIG. 4 also shows a shaft 143 that contains separate guidewire and inflation channels (not shown) leading to the balloon 24 via the brachial artery or alternative access points as understood by the skilled addressee, and then the axillary artery. Also shown is a shaft 145 containing separate guidewire and inflation channels leading to the balloon 24, also via the brachia, artery and then the axillary artery 144, and an end 146 of the shaft 145.

With reference to FIG. 4, it is within the scope of the present invention that other arteries, for example the internal thoracic artery to be infused.

Figure 5:
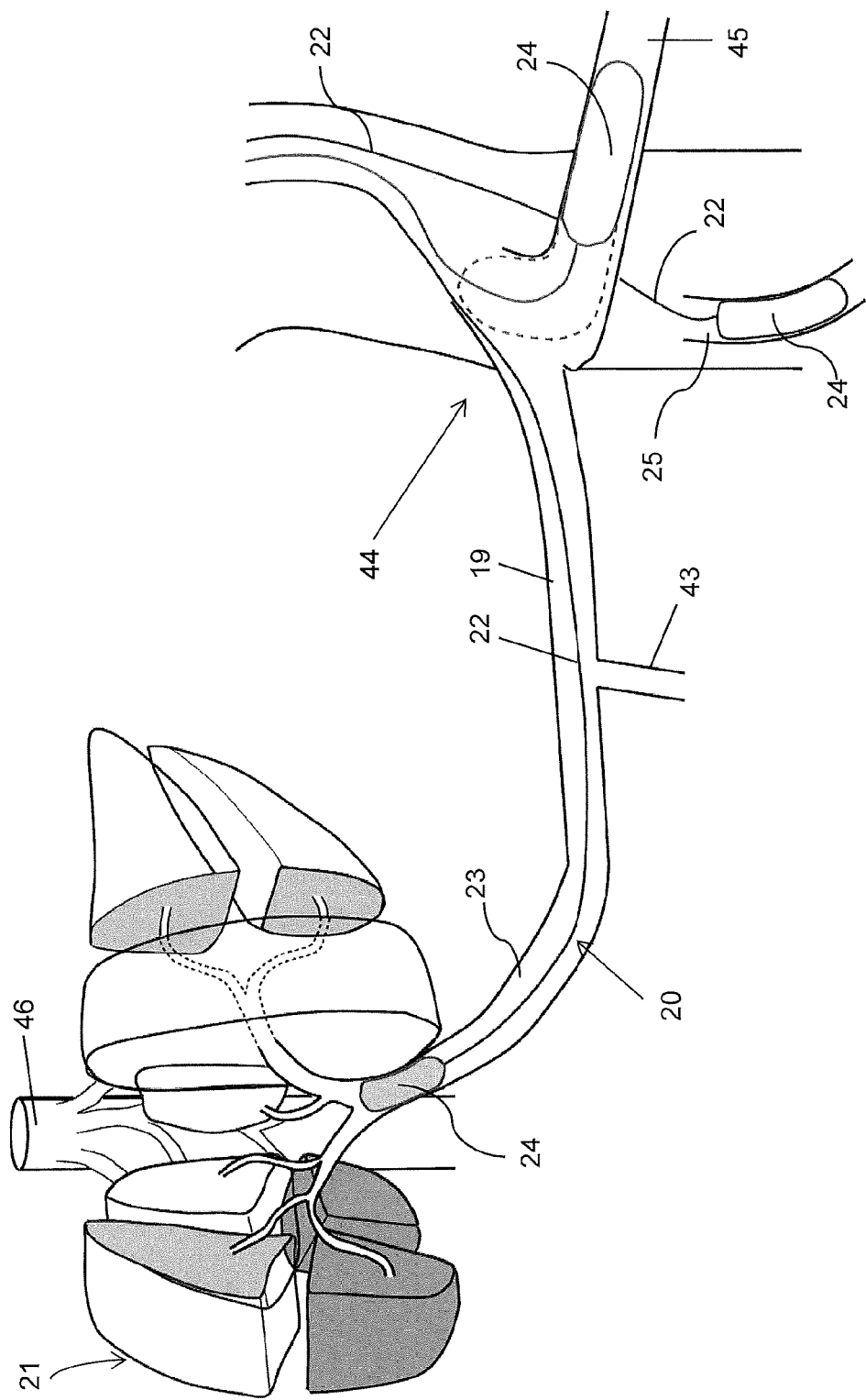
FIG. 5 is a schematic representation of an arterial occlusion balloon positioning arrangement of balloon catheter systems for control of vascular flow to the liver according to an embodiment of the present invention.

FIG. 5 shows an arterial occlusion balloon positioning arrangement 20 of a balloon catheter system for vascular isolation of the liver 21. Three catheter balloons 24 on catheter lines 22 are inserted into the blood vessels 23 supplying blood to and from the liver 21. Balloons 24 are placed in a number of the superior mesenteric artery 25, the gastroduodenal artery 43, the common or proper hepatic artery 23, and the splenic artery 42, 46 is the inferior vena cava and 44 is the coeliac axis.

Figure 6:
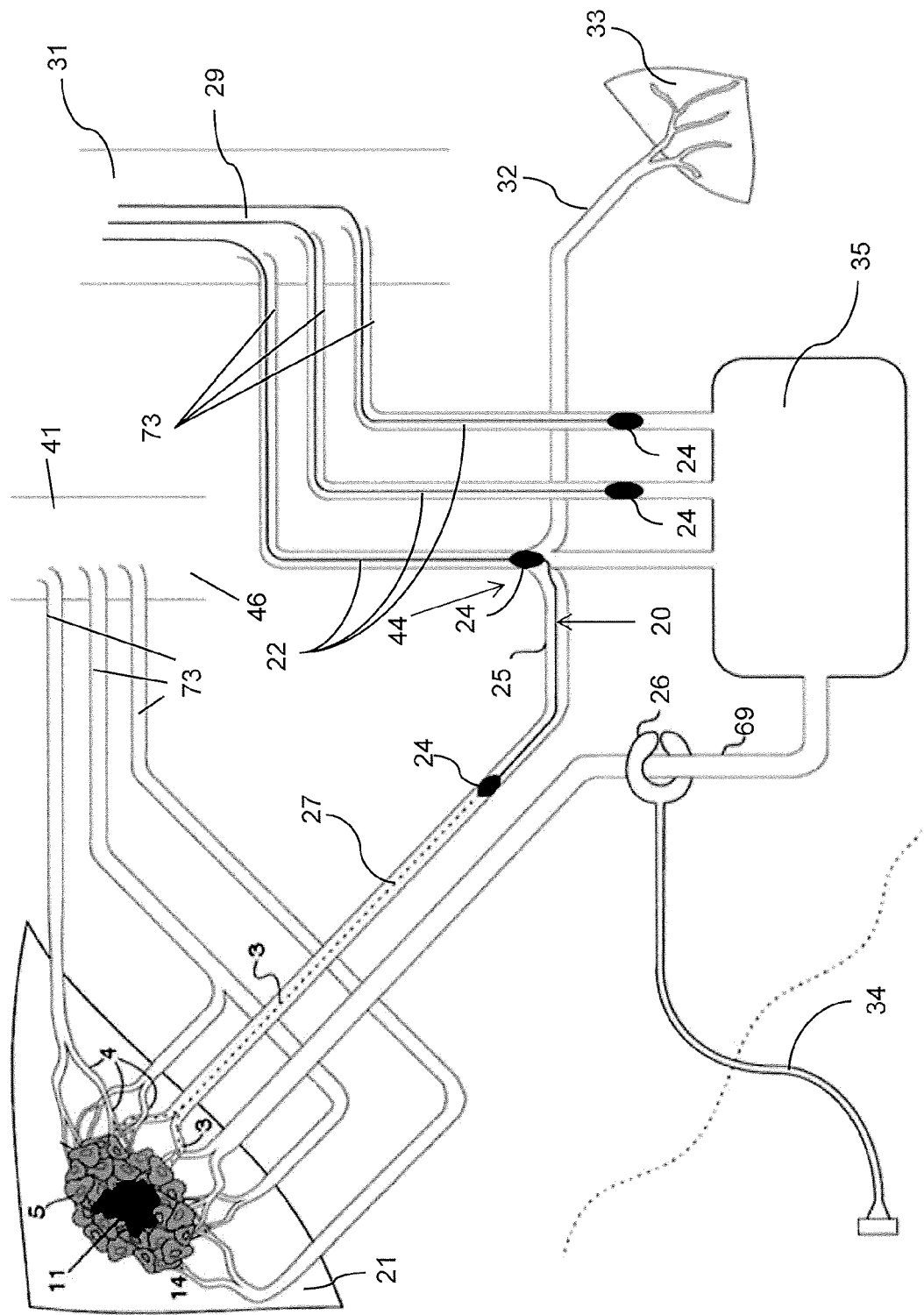
FIG. 6 is a schematic representation of an arterial occlusion balloon positioning arrangement of balloon catheter systems which provides control of collateral arterial blood flow for use in hyperperfusion of the liver according to an embodiment of the present invention.

FIG. 6 shows an example of vascular isolation of the liver 21 to treat a tumour 11 by the positioning of an inflated occlusion balloon 24 in the hepatic artery 23 and by a microcatheter 3 that is located through a central guidewire channel of the occlusion balloon 24 and extends to an opening inside the hepatic artery 23. The microcatheter 3 is so formed that it wedges inside the vessels supplying the tumour 11 and, by the forcing of the walls of the microcatheter 3 against the walls of the vessels supplying the tumour, it obstructs flow through the arterial collaterals. The umbra or flow shadow is dense due to the double obstruction minimising the flow to the tumour 11. The portal collaterals are also obstructed by balloons 24 which are either intravascular or exovascular surrounding the celiac axis 44, superior mesenteric artery 25 and inferior mesenteric vessels, respectively. The result is a low arterial flow in the intestines 35 with secondary low flow through the portal vein 69 which further decreases the flow to the tumour 11. In one embodiment, this flow can be further decreased by inflating an implantable cuff 26 around the portal vein 69. This method of vascular isolation also increases the ischemic effect, thereby inducing central necrosis in the tumour 11, which has a growing edge 5. The interstitial fluid flow in the lymphatics 4 from the tumour 11 is increased by increasing the pressure in the hepatic veins 73 and inferior vena cava (IVC) 46 through controlling the positive end expiratory pressures (PEEP). The outward flow from the tumour 11 can be controlled by varying the PEEP. Alternatively, three separate balloon 24 catheters 22 can be positioned to occlude the three hepatic veins 73, respectively.

Balloons in the coeliac, gastric, superior and inferior mesenteric arteries, one or more in combination when occluded will produce a decrease in portal venous flow. There is a physiological response defined as hepatic artery buffer response (HABR). This results in a substantial increase in hepatic artery flow mediated by nitric oxide adrenalin and other local humeral substances. In delivery of therapeutic substances, stem cells, nanoparticles, chemotherapy or radio-active particles, it may be efficacious in activating the HABR.

It is within the scope of the present invention for alternative forms of restriction than an inflatable cuff for flow restriction, such as a tourniquet or otherwise.

Figure 7:
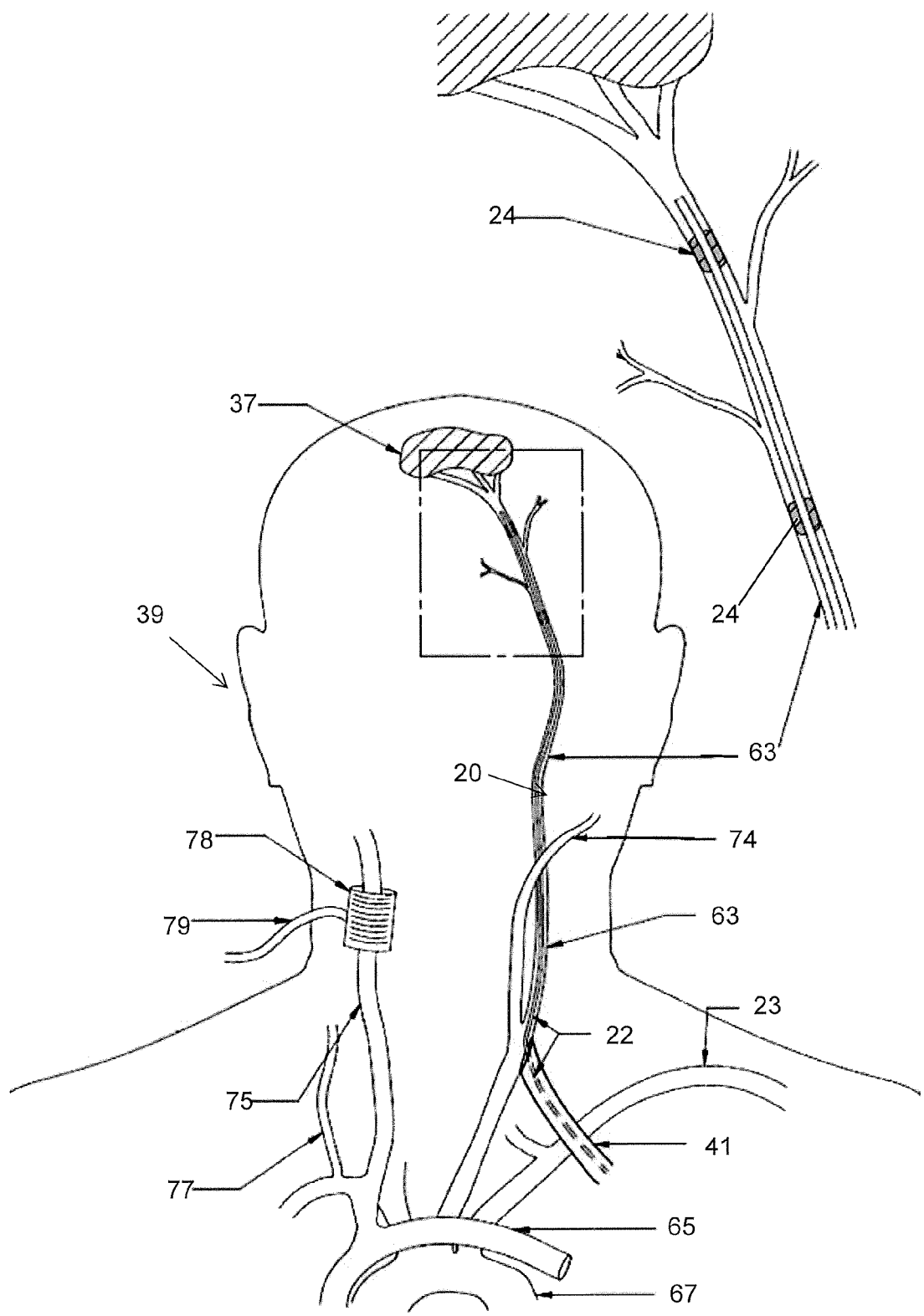
FIG. 7 is a schematic representation of vascular occlusion balloon positioning arrangement according to an embodiment of the present invention for treatment of the cranial region.

FIG. 7 shows an embodiment of the present invention applied to the vascular and arterial isolation of the cranial region 3a This may include tumours 37 of the brain or carcinoma of the tongue, larynx, pharynx, spacial skin and submandibular glands.

In one embodiment, the site of origin of the therapy is an access device 41 at the origin of the external carotid artery 74 or it can be from either or both groins or arms. The access device can be implanted unilaterally or bilaterally. Access device 41 is implanted bilaterally for structures receiving close to midline blood supply. For inflow, the main axis is super selected to the target area and controlled with endovascular or extravascular balloon 24 occlusion systems on catheters 22 as described above. In some situations the occlusion system is related to the excellent collateral flow of a proximal and distal balloon 24 systems (co-rail systems are required to reduce pressures that correspond to the critical closing pressures which are 20 mmHg at a pre capillary level).

For collateral control, other branches of the external carotid 74 may need to be cannulated depending on the radiological appearance and the pressures obtained after occluding the main axis. Other neighbouring branches of the external carotid may be required to be controlled including the branches of the subclavian vessels such as the costocervical and thyrocervical trunks.

Outflow control is achieved by postural manoeuvres (such as moving into the Trendelenburg position), positive and expiratory pressures and occlusive catheters in the internal jugular vein 75, common facial or anterior jugular vein which may involve endovascular or external vessel occluding systems.

Internal occlusion of the internal jugular vein is achieved with a balloon 24 catheter 22 as described above. External occlusion is achieved with an extravascular occlusion device 78 that applied pressure to the outside of a vein via an inflation line 79.

The external occlusion with extravascular occlusion device 78 is applied to the same blood vessel that the access device is applied to, on the same side. That the occlusion device 78 is illustrated on the contralateral side in FIG. 7 indicates that bilateral use.

The venous pressures are continuously monitored. Once control of the vessels is contained, the plasma proteins and blood are washed out from the targeted segment and replaced with the saline containing therapeutic agents. With reestablishment of flow the collateral and main axis arterial inflow may be deflated first and the venous outflow control continues for 5-20 minutes to minimise systemic recirculation. With the plasma proteins washed out the action of the patient's antibodies is greatly reduced or eliminated. With the action of the patient's antibodies in the target segment being eliminated or reduced the chances of an immune response in the target segment is greatly reduced or removed.

There are several constraints in the treatment of delivery of therapeutic agents into the parenchyma of the brain. The blood brain barrier (BBB) prevents more than 95% of therapeutic substances traversing the endothelium. Molecules less than 500 Daltons are usually able to cross. The problem is the tight junctions between endothelial cells do not allow free movement across this barrier. The next problem related to the tumours themselves as they tend to be diffuse rather than being focused in a specific mass. In regard to the fluid flux this is associated with an increase in intracranial pressure which may induce symptoms associated with the syndrome of intracranial hypertension. The next problem relates to the relative brain ischemia, particularly with focal infusions. The isolation treatment would best be done under local anaesthetic to modulate the infusion time. The last problem is the good collateral flow in some parts of the brain which is difficult to produce oncotic gradients as there is difficulty in washing out the oncotically active plasma proteins in the infused segments. The last problem relates to the difficulty of increasing the outflow pressure so that there is net movement from the intravascular to the extravascular space.

For segmental brain isolation, establishment of inflow control is via arterial access via the groins external carotid artery 74 or the arm arteries. Collateral flow is minimised by the use of a collateral, so a co-rail system where one balloon is proximal in the larger vessel and the second one closer to the lesion usually in the same vessel, and infusion proceeds down the central or guidewire channel. Outflow cerebral hypertension can be improved by Trendelenburg or specific obstruction to the internal jugular vein either endovascularly, with occlusive balloon systems, or extravascular occluding system implanted around the internal jugular vein in the neck. This system can be activated and de-activated transcutaneously.

The plasma proteins and blood are washed out from the segment and replaced by the active therapy. This may be aided by using hypertonic carrier solution to shrink the endothelial cells therefore increase the endothelial pore size. Another possibility is to use other carrier substance particularly if a lipophilic agents which traverse the blood brain barrier easier.

Figure 8:
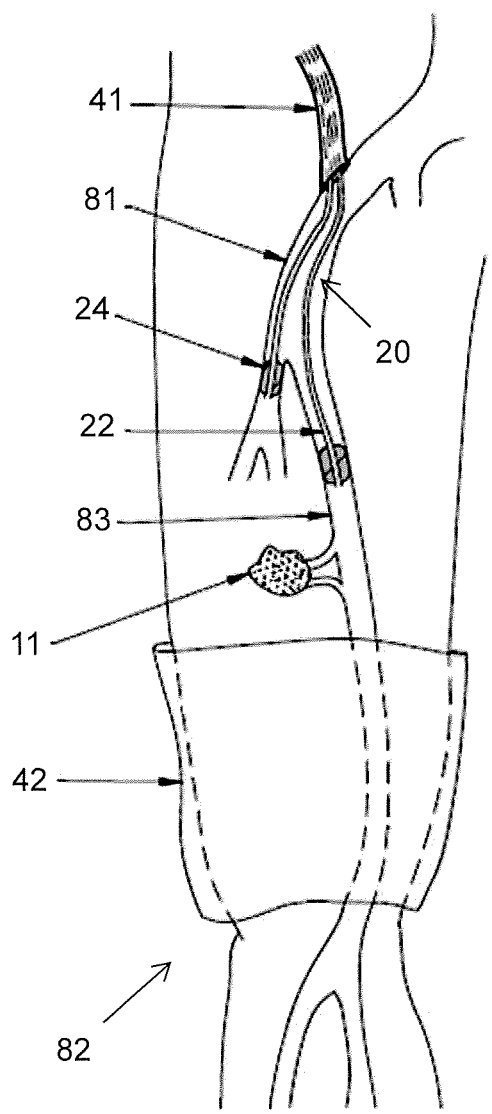
FIG. 8 is a schematic representation of an arterial occlusion balloon positioning arrangement for control of vascular flow to the lower limbs according to an embodiment of the present invention.
Figure 9:
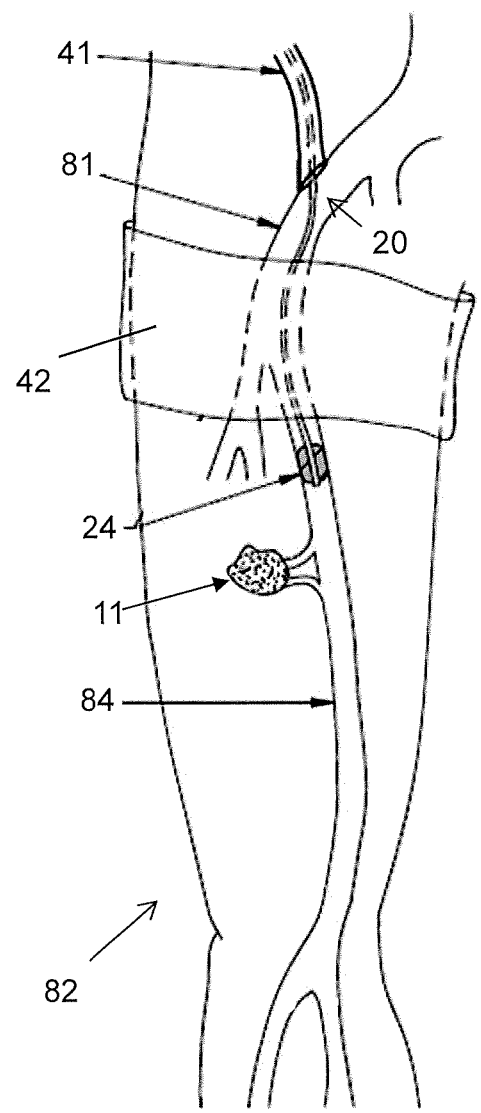
FIG. 9 is a schematic representation of an arterial occlusion balloon positioning arrangement for control of vascular flow to the lower limbs according to an embodiment of the present invention.

FIGS. 8 and 9 illustrate the methods and devices for vascular isolation of the present invention applied to the lower limbs 82. FIG. 8 illustrates arterial isolation and FIG. 9 illustrates venous isolation. The site of origin of endoluminal catheters may be on the contralateral limb in the common femoral or auxiliary or even brachial vessels or via an arteriovenous fistula. If the lymphatic systems cause occasion to be treated then controlling systems may position proximal to the lymphatic nodes i.e. the iliac systems. In some situations implantable extra vascular occlusive systems can be used.

The skilled addressee will readily recognise that the methods and devices for vascular isolation illustrated in FIGS. 8 and 9 are readily applied to the upper limbs.

The skilled addressee will understand that the site of origin of the therapy is an access device 41 at the origin of the common femoral artery 81 or it can be from either or both groins or arms.

Individual control of the profunda vessels or internal iliacs or co-rail systems is achieved via use of balloons 24 over a catheter line 22 as described above to isolate the tumour 11. In the embodiment of FIG. 8 a balloon 24 is placed in the superficial femoral artery 83. In one embodiment, this is monitored by the appropriate pressure transduction. In the embodiment of FIG. 9 a balloon 24 is placed in the superficial femoral vein. Outflow control can be aided by reverse Trendelenburg positioning. Endovascular balloons either ipsilateral or contralateral or tourniquets 42 may be appropriate in some cases and also positive and expiratory pressure can be added. Any or all of the above mechanisms may be used to control outflow. Plasma and blood removal of oncoticly active material and replacement by therapeutic substances in biocompatible solution, resumption of the normal circulation may be delayed by removing the outflow obstruction several minutes after the inflow control system. Control of the profunda vessels can be achieved ipsilaterally or contralaterally.

Figure 10:
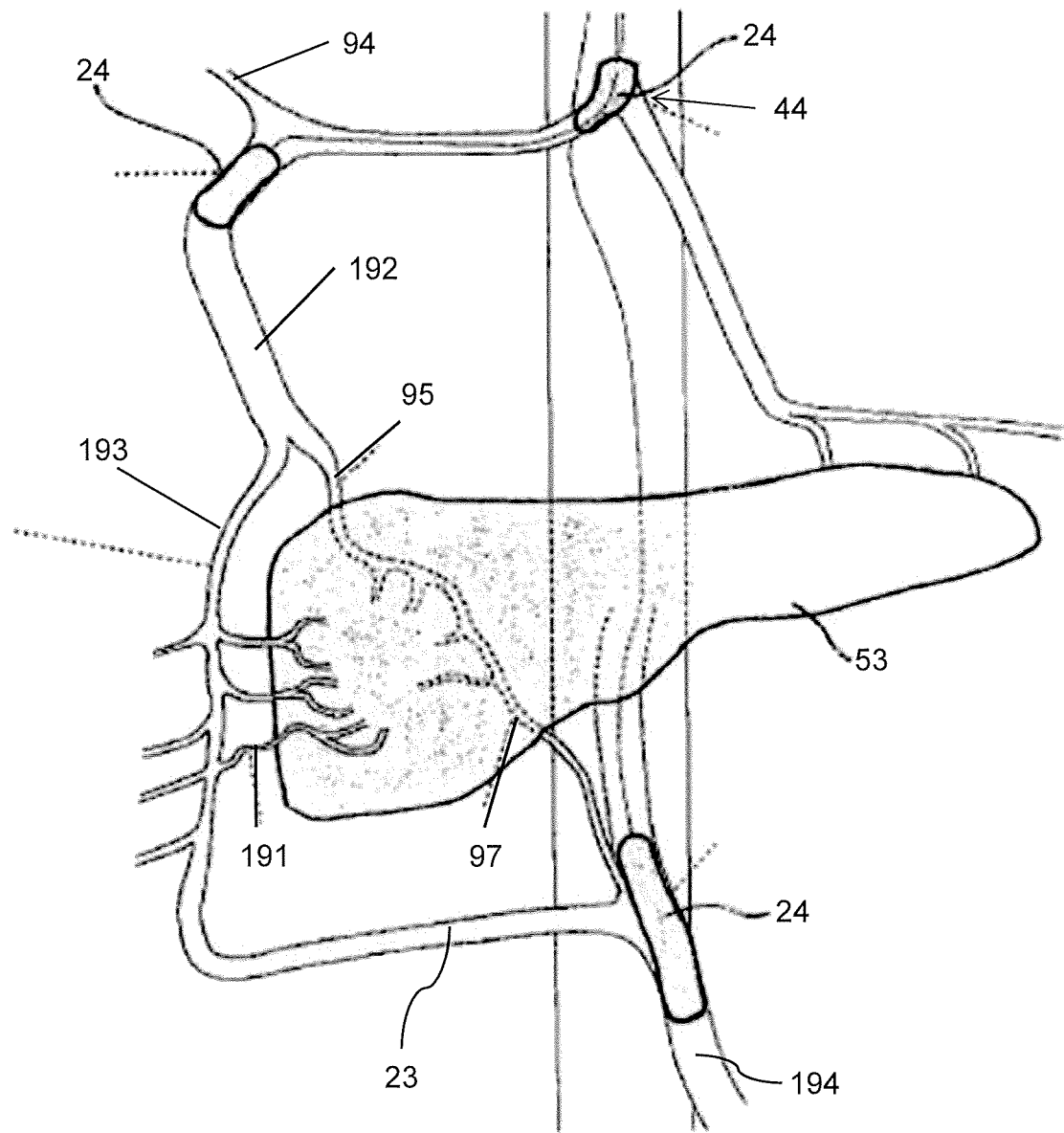
FIG. 10 is a schematic representation of an arterial occlusion balloon positioning arrangement of three separate balloons in catheter systems which provide control of vascular flow to the pancreas according to an embodiment of the present invention.

FIG. 10 shows an arterial occlusion balloon positioning arrangement of three separate balloon 24 positions of the balloon positioning arrangement 20 for vascular isolation of the pancreas 53 through the anterior superior pancreaticoduodenal artery 193, is the anterior inferior pancreaticoduodenal artery 191 and the posterior superior pancreaticoduodenal artery 95. Also shown are the posterior inferior pancreaticoduodenal artery 97, the superior mesenteric artery 194 the gastroduodenal artery 192, the proper hepatic artery 94 and the coeliac axis 44.

Figure 11:
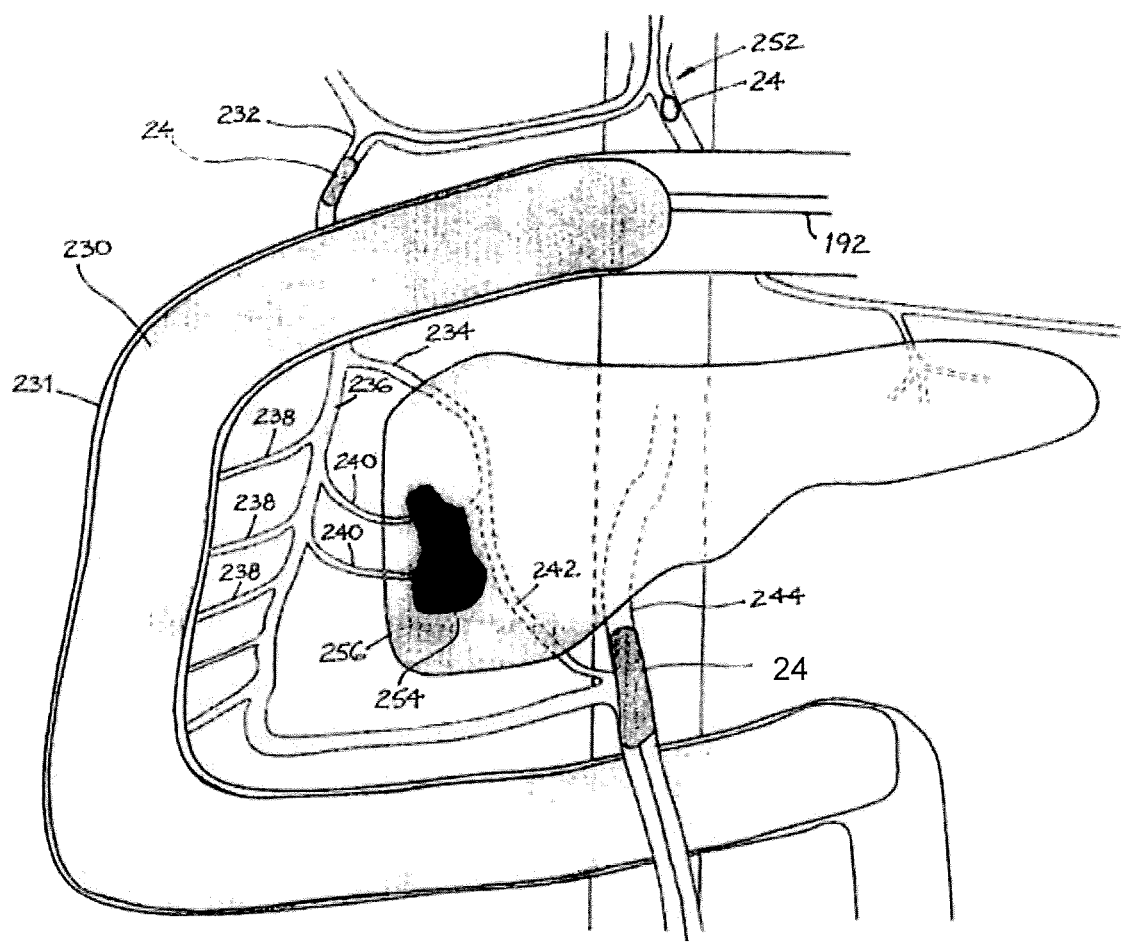
FIG. 11 is a schematic representation of a pressure controlled intraluminal balloon and a connecting distal end of a multi-channel catheter shaft system according to another embodiment of the present invention; for use in the duodenum for vascular isolation of a tumour in the pancreas according to an embodiment of the present invention.

FIG. 11 shows an example of an inflated mucosal compressive balloon 230 positioned in the duodenum 231 used in an embodiment of the balloon positioning arrangement 20 of the present invention. Also shown is the superior pancreatic duodenal artery 232, its posterior branch 234, and its anterior branch 236. Also shown are the gastroduodenal arteries 238 and the pancreatic branches 240 from the anterior branch 236 of the superior pancreatic duodenal artery 232.

Both the posterior branch 234 and the anterior branch 236 communicate with the posterior and inferior pancreatic duodenal branches 242 which usually arise from the superior mesenteric vessel 244. Balloons 24 are positioned in the splenic origin 252, the superior pancreatic duodenal artery 232 and the superior mesenteric vessel 244, respectively. A pancreatic tumour 254 is shown in the head of the pancreas 256. The inflated mucosal compressive balloon 230 traverses all four portions of the duodenum 231.

As the pancreas 256 is now isolated, infusion of a chemotherapeutic agent to treat the targeted area (or tumour) can occur.

The outer infusion balloon of the mucosal balloon 230 may be filled with ice water. Ice water has the effect of compressing of the blood vessels of the duodenum and has a secondary effect of prolonging ischemic time by minimising the effects of hypoxia, i.e. "cold ischemic time" is longer than "warm Ischemic time" Cold temperature also produces vasoconstriction of the small blood vessels of the duodenum and this also protects against infusion of cytotoxic drugs. The blood vessels in the tumour 254, however, have little or no vasomotive tone owing to the absence of smooth muscle and nerves within the vessel walls. As there is a continuous heating effect from surrounding structure (albeit minimised due to the decreased blood supply); to maintain the required cold temperature of the balloon 230, a continuous infusion of temperature controlled fluid is required to allow constancy of the ambient duodenal temperature. Varying the PEEP can increase the venous pressure in the liver and portal system so as to minimise leakage of the chemotherapeutic agent into the systemic circulation. Similarly, direct balloon obstruction of the hepatic veins can increase venous pressure.

As tumour vessels do not react to cold in the way that other tissue does, the use of ice water allows targeting of tumour whilst avoiding delivery of therapeutic substances to the duodenum due to the mucosal tissues response to the ice water.

Figure 11A:
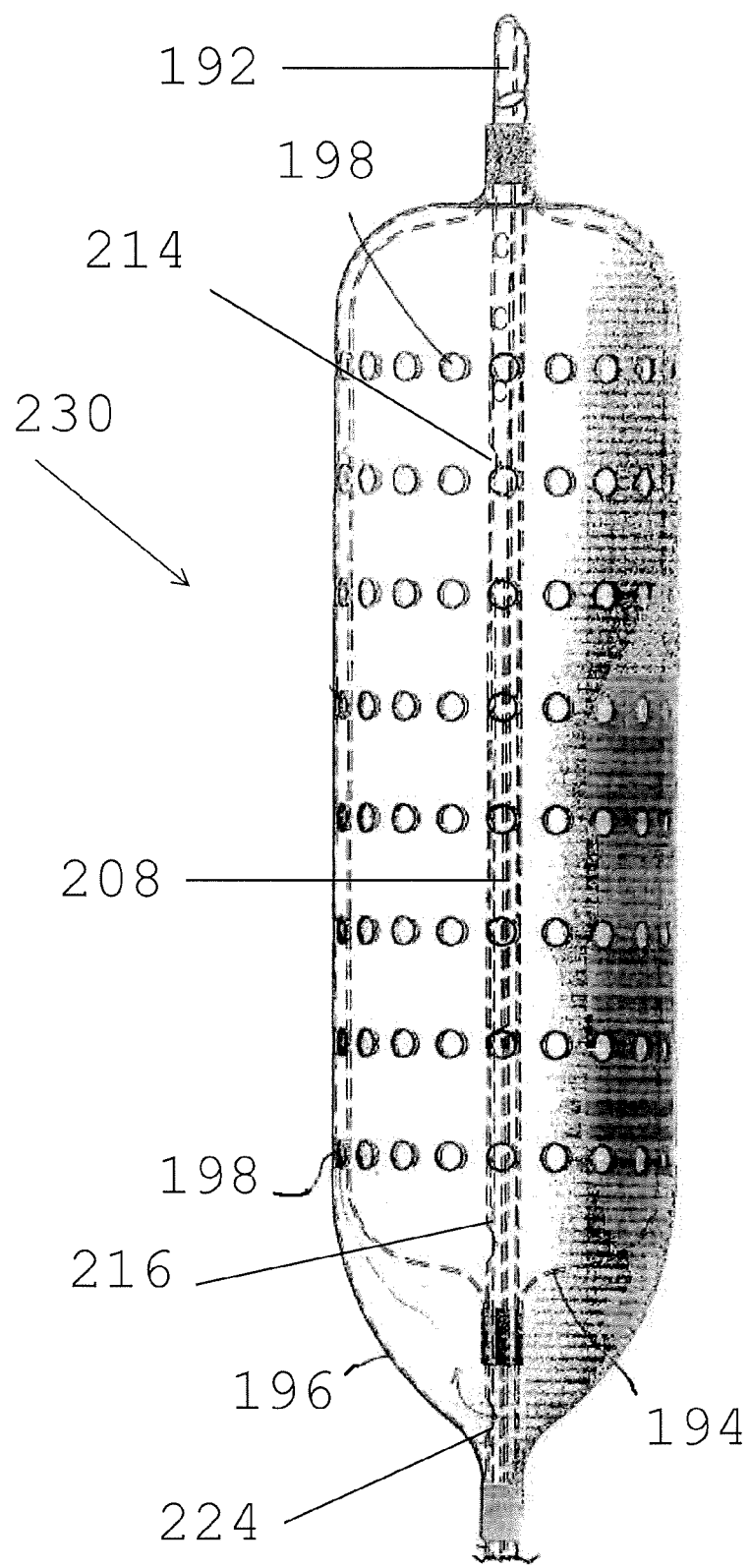
FIG. 11A is a side view of the compressive balloon of FIG. 11.

FIG. 11A illustrates the mucosal balloon 230 in further detail. A multi-channel catheter 192 passes through the mucosal balloon 230. The mucosal balloon 230 includes an inner inflation balloon 194, adapted to be pressurised, and an outer infusion balloon 196 adapted to contain or transfer vasoconstrictive agents or cold fluid to surrounding tissue through elution ports 198. Temperature controlled fluid is injected into the inner balloon 194 through aperture 214 in a channel of catheter 192 and inflation fluid (such as air) is injected into inner balloon 194 through aperture 216 in a second channel of catheter 192 to inflate and maintain pressure in the inner balloon 194. Therapeutic substances are injected into the space between inner inflation balloon 194 and outer infusion balloon 196 through aperture 224 in a third channel of multi-catheter 192. The therapeutic substances are transferred through elution ports 198 into the surrounding tissue and the cold temperature assists the targeting of tissue such as tumour tissue.

Figure 12:
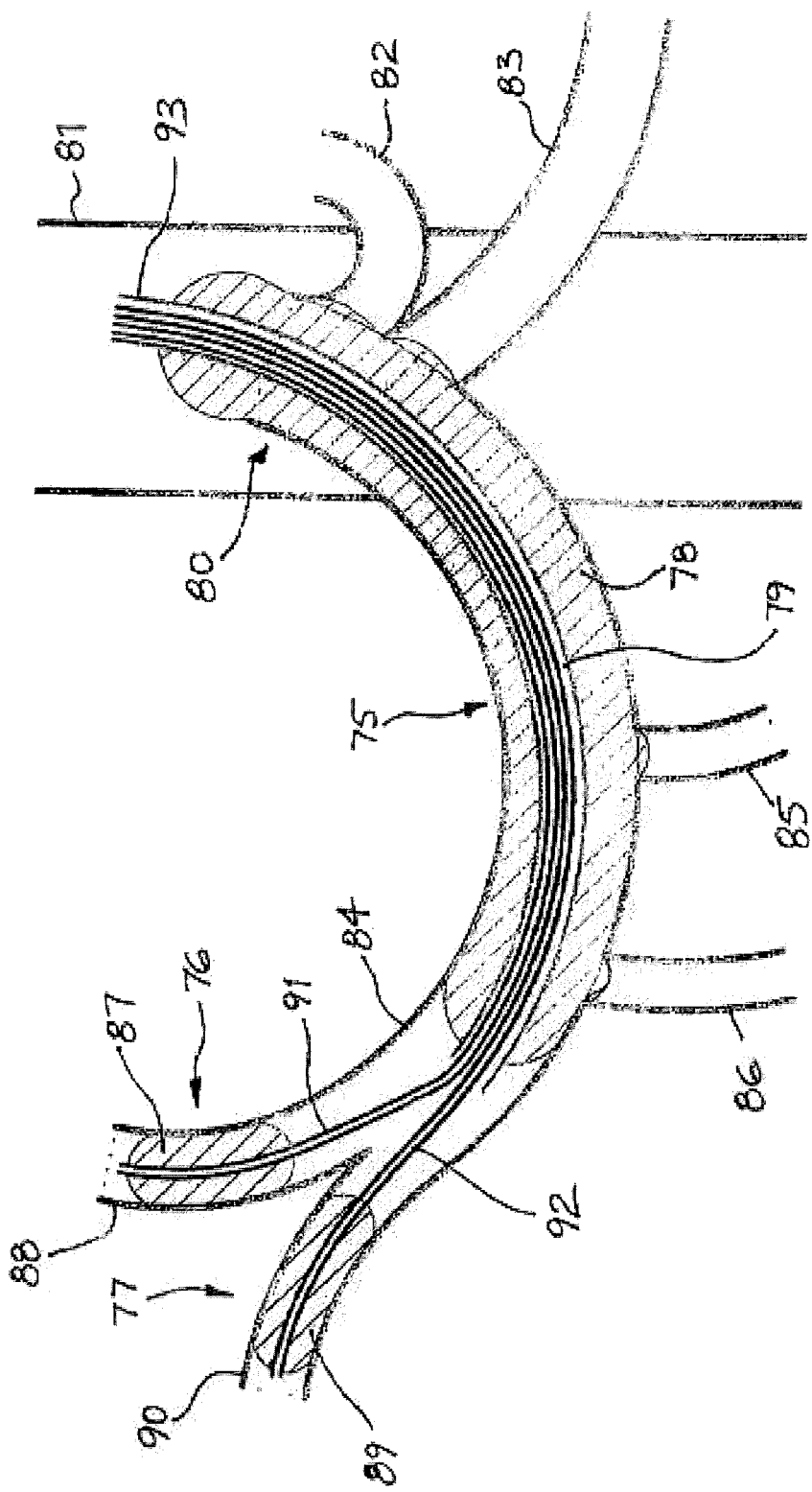
FIG. 12 is a schematic representation of an arterial occlusion balloon positioning arrangement of a three separate balloon catheter system, and which provides control of collateral arterial blood flow for use in hyperperfusion of the liver.

FIG. 12 shows an arterial occlusion balloon positioning arrangement of three separate balloon catheter systems 75, 76, 77 to minimise collateral blood flow and optimise hyperperfusion in the liver. The balloon 78 of the system 75, which is a soft and malleable balloon, has a lumen 79. The balloon 78 extends longitudinally beyond the coeliac axis 80 into the aorta 81 and also stretches into the opening of the left gastric artery 82, the splenic artery 83 and the other collateral vessels of the common hepatic artery 84, such as the right gastric artery 85 and right gastroepiploic artery 86 and many small vessels. The balloon 87 of the system 76 is positioned in the left hepatic artery 88 and the balloon 89 of the system 77 is positioned in the right hepatic artery 90. The two separate catheters 91, 92 for each balloon 87, 89 are capable of being passed through the internal diameter of the lumen 79 provided by the wider catheter 93 for the balloon 78.

The balloon positioning arrangement shown in FIG. 12 allows for optimal delivery of therapeutic agents by control of inflow from the common hepatic artery 84 and from collateral vessels. The balloon 78, when inflated, is at least 5 cm long but may be up to 40 cm long to occlude as many collateral vessels as possible. R is malleable to conform to the native vessel (i.e. the common hepatic artery 84) and to protrude partly into the openings of collateral vessels. The lumen 79, which also defines the central guidewire channel, has a larger diameter than guidewire channels of the prior art. As a result, the lumen 79 can act like a stabilising sheath. This will allow the balloon 78 and other such balloons to be used for isolation and occlusion of vessels which branch off very acutely from main vessels.

A common method for inserting balloon catheter systems into acutely angled vessels involves a guidewire being initially inserted into the vessel and then a balloon catheter system being inserted over the guidewire to the desired position. However, when the guidewire is removed in order to allow for inflation of the balloon and subsequent infusion of therapeutic agents, the uninflated balloon may slip out of the vessel. This problem may be avoided by use of the long collateral balloon 78 shown in FIG. 12 in which the lumen 79 acts like a stabilising sheath, even when the balloon is uninflated. The guidewire can then be removed, and additional collateral balloon systems can then be inserted through the lumen of the long collateral balloon. Alternatively, the guidewire may be removed after the long collateral balloon is inflated. In that case, because the balloon 78 is quite malleable and protrudes partly into the openings of collateral vessels, it produces greater frictional resistance forces so that, when the guidewire is removed, the inflated balloon does not slip out of the vessel.

The lumen or central guidewire channel of most prior art balloon catheter systems are 0.035 inches or 0.038 inches in diameter. However, the balloon catheter system 75 employing the balloon 78 is capable of allowing two separate balloon infusion catheter systems to be passed through its lumen which each have a minimum diameter of 0.039 inches.

Figure 13:
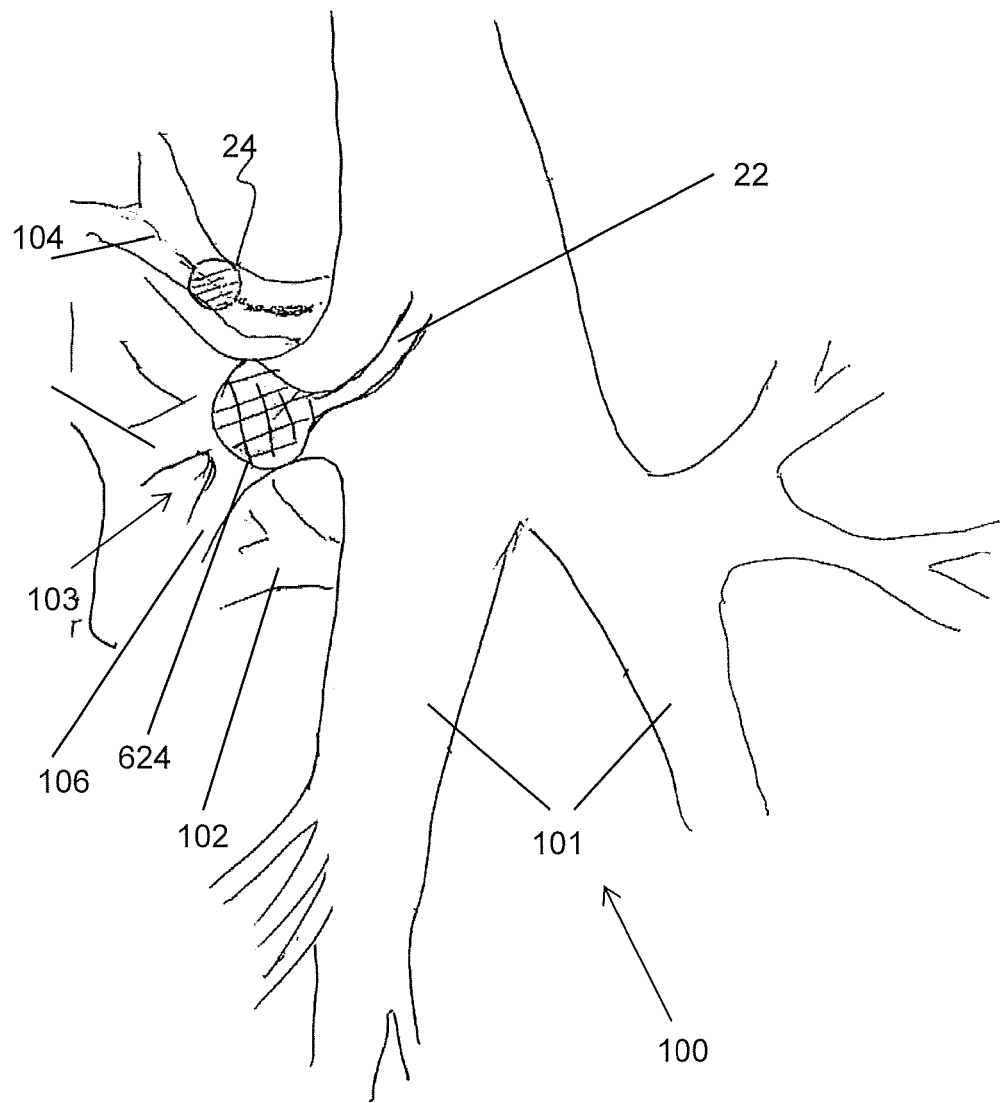
FIG. 13 is a schematic representation of vascular isolation of the upper lobe of the lung.

The balloon positioning arrangement shown in FIG. 13 illustrates a mechanism of isolation and infusion of the right upper lobe of the lungs 100. The main bronch 101 and the pulmonary vein 102 are shown. The skilled addressee will readily recognise that any part or the whole of either lung can be isolated in a similar manner.

Non ventilation of a lung or segment leads to atelectasis or collapse of that lung or segment. Vasoconstriction of the pulmonary arteries follows physiologically in order to shunt blood to aerated segments. The blood flow of tumours are not as responsive to vasoconstriction related to their primitive nature hence the degree of vascular cell activity compared to normal tissue for selective infusion purposes. Some of the blood supply may come from brachial arteries which are less affected. Related to the atelectasis the pulmonary venous pressure increases which may be aided by PEEP.

Consequently the treatment for primary or secondary lung neoplasia in the right upper lung 100 according to the present invention is:
  (a) induction of atelectasis via non-ventilation by balloon occlusion of bronchus;
  (b) introduction of super selection catheters 624 with balloon 24 occlusion of the pulmonary artery 103 at the apical segment 104, and the anterior segment 106 from peripheral venous access;
  (c) washout of oncologically active material from the supplying vessels to the isolated lung lobe or segment;

(d) application of PEEP; and
(e) infuse active therapy up to a projected pulmonary venous pressure.

The lungs are approximately 450 g (right) and 400 g (left); the right has 3 lobes. Projected mass ratio advantage in a 75 kg patient who is approximately 600 times to a lobe. Collapse of the whole lung can be performed whilst infusion only of an affected segmental part as required by the anatomical distribution of the tumours.

In addition to the above discussed applications the balloon positioning arrangement of the present invention can also be used in the following applications.

Head and Neck Lesions

This may include tumours of the nasal, pharynx and larynx, the tongue, floor of mouth, sinuses, submandibular glands and malignant areas of the skin and mucous membrane. The usual site of origin of the therapy is a multi-access port at the origin of the external carotid or it can be from either or both groins or arms. Access device is implanted bilaterally for structures receiving close to midline blood supply. Inflow, the main axis is superselected to the target area and controlled with endovascular or extravascular balloon occlusion systems and in some situations related to the excellent collateral flow a proximal and distal balloon systems (co-rail systems are required to reduce pressures that correspond to the critical closing pressures which are 20 mm Hg at a pre capillary level).

Other branches of the external carotid may need to be cannulated depending on the radiological appearance and the pressures obtained after occluding the main axis. Other neighbouring branches of the external carotid may be required to be controlled including the branches of the subclavian vessels such as the costocervical and thyrocervical trunks.

The Outflow Control

This is achieved by postural manoeuvres such as Trendelenberg, positive and expiratory pressures and occlusive catheters in the internal jugular vein, common facial or anterior jugular vein which may involve endovascular or external vessel occluding systems. The venous pressures are continuously monitored. Once control of the vessels is contained, the plasma proteins and blood are washed out from the targeted segment and replaced with the saline containing therapeutic agents. With reestablishment of flow the collateral and main axis arterial inflow may be deflated first and the venous outflow control continues for 5-20 minutes to minimise systemic recirculation.

Vascular Isolation and Onconic Manipulation of Lesions in the Pelvis

This may include lesions in the bladder, rectum, vagina, anal canal, prostate, uterus, cervix, lymphatics and other primary or secondary lesions. The site of origin of the catheters are the vascular access systems located in one or other or both groins may include the common femoral, superficial femoral systems and similarly the venous access system located in the common femoral, superficial femoral, external and iliac vein. Occasionally control of the great saphenous vein is required. The actual inflow may be controlled at two levels with superselection of the target organ e.g. the inferior vesical artery for prostate lesions with another balloon which controls the origin of the internal iliac system. As these organs receive blood flow bilaterally, synchronous control of the contralateral main axis with superselection can be achieved by guiding catheters placed retrograde over the bifurcation of the aorta. The pressures monitored are the superselected end pressures transduced on both sides individually and then together and similarly the collateral pressures again measured unilaterally then bilaterally. These measurements determined the need for simultaneous contralateral flow control. In some cases embolisation of significant collateral vessels may be required to obtain adequate inflow pressure reductions.

Outflow Control

Outflow control is achieved by simultaneous occlusion of the internal, external or selected pelvic vein, iliac vein or veins. Elevation of the venous outflow pressure may be achieved by both postural manoeuvres (head up) and in addition to the positive and expiratory pressure (PEEP).

Oncotic Manipulation

The blood is removed from the isolated organ to be treated and replaced with the appropriate chemotherapeutic or other form of treatment in hypo-oncotic solution. To maximise retention the venous pressures remain elevated by all means for 5-20 minutes after the resumption of normal arterial flow.

Methods of Isolation and Fluid Flux Control to the Pancreas

The main axis arterial inflow is controlled by catheters and balloons in the common hepatic with superselection of the gastroduodenal or superior pancreaticoduodenal. Other lesions in the pancreas may require the splenic vessels or pancreatic magna to be the main axis control system and occasional superselection of the inferior pancreaticoduodenal is required. The collateral control is via balloon systems controlling the gastric the gastroepiploic, hepatic vessels and the splenic artery depending on the site of target tumour.

Venous Obstruction

This is obtained by positive and expiratory pressure (PEEP) as well as an extra vascular occlusive device surrounding the portal vein or in some cases the splenic vein. The hepatic veins may also require control via balloons. This degree of occlusion controlled transcutaneously, radiologically. After vascular isolation the plasma proteins and blood are washed out from the isolated segment and replaced with saline containing the chemotherapeutic agent. Monitoring of the collateral as well as the main axial pressures and radiologically the placement of the appropriate catheters is mandatory. Offline measurement of chemotherapeutic activity and levels is also helpful with management and in some cases a method shielding of the surrounding mucosa can be obviated by the use of cold infusions in the stomach and duodenum and first part of the duodenum causing reactive vasoconstriction and minimal blood flow.

In Vascular Isolation and Manipulation of Flux of Lesions in the Breast

Inflow Control

The access system is implanted in either arm in the brachial vessels or the groin. For medial lesions, the internal mammary is superselected and occluded and prepared for infusion. In lateral lesions the lateral thoracic vessel is superselected. In some rare cases the medial and lateral pectals can be isolated with 2 balloons proximal and distal to their origins. Collateral vessels, the other vessels that are not superselected i.e. the internal mammary, medial and lateral pectoral, thyrocervical trunk, costocervical trunk, and lateral thoracic vessels have occluded as required depending on the site of lesion. One single or two balloons are often sufficient to occlude all collateral inflow with appropriate pressure reduction.

Outflow

The outflow cannula's originate from the brachial and occlude all of the tributaries of the subclavian and axiliary vessels. Therefore the lateral thoracic vein, the medial and lateral pectoral veins, the veins from the thyrocervical and costcervical trunks and internal mammary vein are all occluded simultaneously. Any venous and arterial pressures are monitored both in the main axis and collateral pressures. The arterial systems are then occluded, the plasma proteins are then washed out and then the outflow balloons are inflated and the closed segment is replaced by saline containing the therapeutic agents.

Reconstitution

Is release of the collateral balloons first the main axial balloon and then followed by the venous outflow occlusive systems which are deflated 5-20 minutes after an arterial reconstitution to minimise therapy entering the systemic circulation.

Upper Limb

Site of origin of the catheters/balloons access system depends upon the site of the original lesion and associated lymphatic drainage and in some cases may originate in the groins. In proximal the inflow control system is placed on the proximal side i.e. the cardiac side of the lesion. This may include a double inclusion of the main axis or the use of a fistula to control inflow to the lesion.

Collateral Flow Control

This may involve proximal and distal balloons in the main axis selective occlusion of radial, ulnar interrosseousor circumflex humeral vessels depending on the site of the lesion and the result of the pressure transduction recordings.

Outflow Control

Positive and expiratory pressure, posture and balloons placed on the cardiac side of the lesion as well as control of the appropriate tributaries to the main venous return axis. These vessels may be the brachial auxiliary or subclavian vessels. Replacement of the blood with biocompatible solutions containing the appropriate therapy. Resumption of circulation, venous outflow may be deflated several minutes after the inflow control system to minimise re-circulation of active therapeutic agents into unwanted areas.

The cannulas, catheters and balloon of the above embodiment can be inserted into the body through one access point into the inflow and outflow blood vessels as required. This reduces the number of access points required making extended use of the embodiment in the body easier and reducing the injection points.

By isolating an extravascular space in the manner discussed above and directing therapeutic substances to target spaces whilst minimising the chances of the therapeutic substances flowing out of the target space the above embodiment allows increased therapeutic treatment frequency.

Broadly, with reference to FIGS. 17 to 24 an embodiment of the present invention relates to a blood vessel access device with a chamfered end to eliminate the creation of dead space when the cannula is inserted into a blood vessel.

Figure 14:
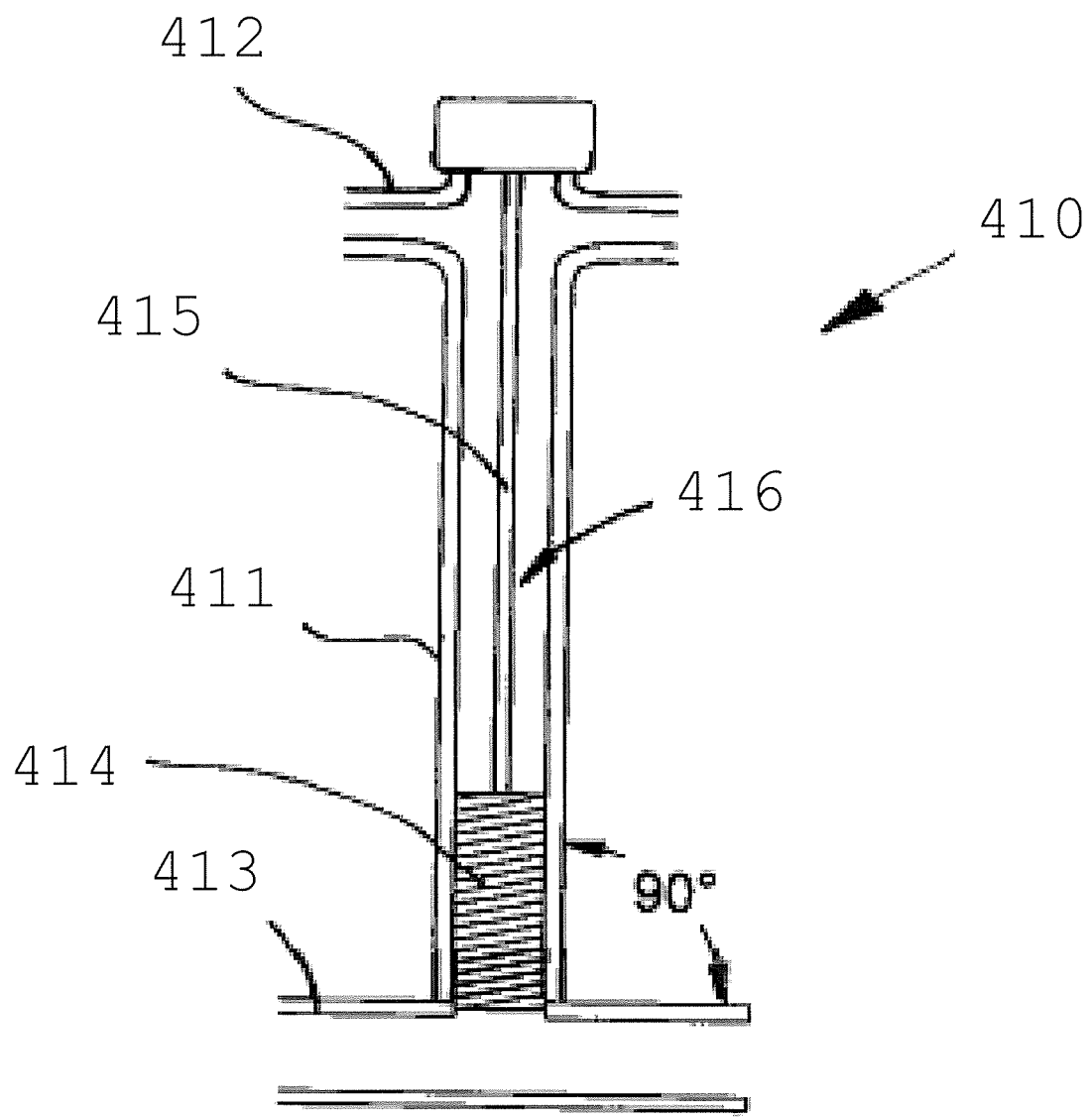
FIG. 14 is a sectional side view of a single lumen access device of the prior art.
Figure 15:
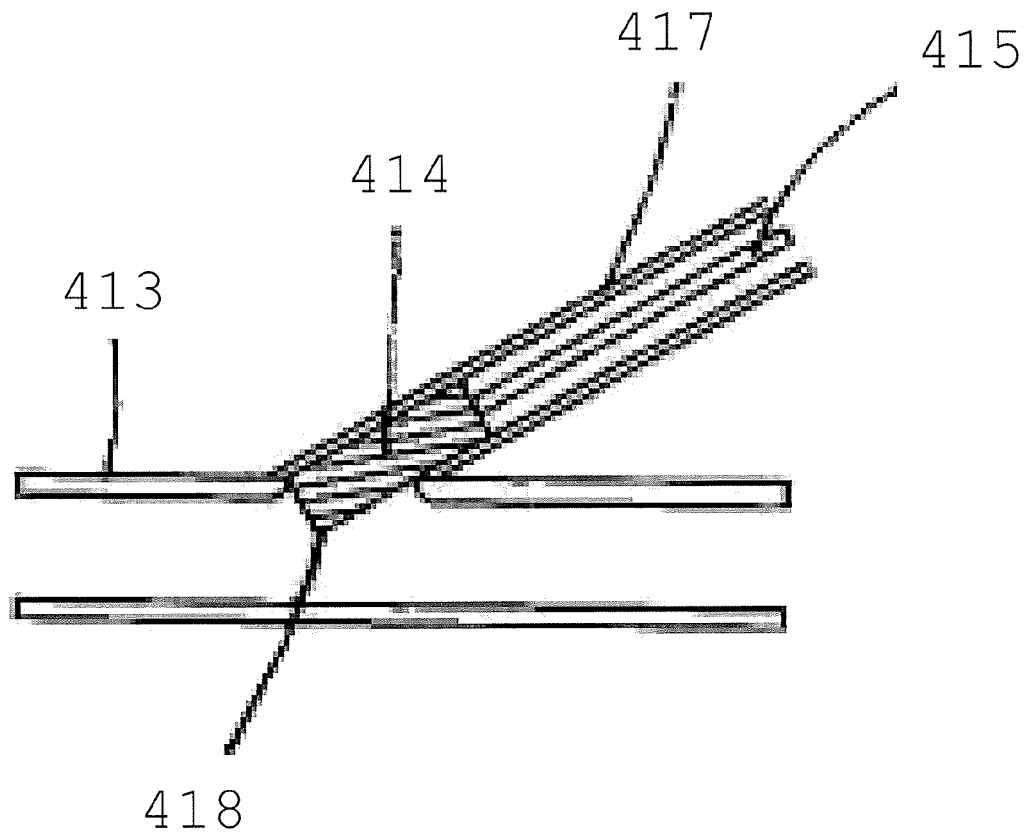
FIG. 15 is a sectional side view of a cannula of another single lumen access device of the prior art, showing the tip of a plunger stem of the device protruding from the cannula into the lumen of a blood vessel of a patient.
Figure 16:
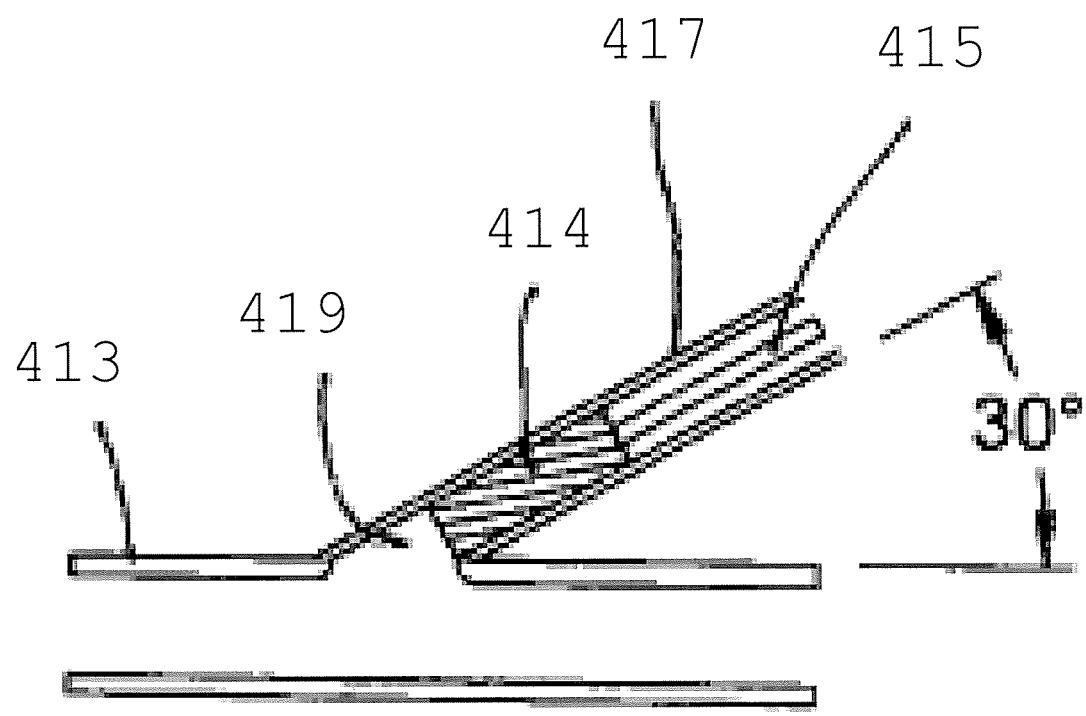
FIG. 16 is a sectional side view similar to that of FIG. 15; but showing the tip of the plunger stem of the device no longer protruding into the vessel lumen but retracted into the lumen of the cannula so as to create a dead space within the lumen of the cannula.

FIGS. 14, 15 and 16 show prior art single lumen access devices. The access device 410 shown in FIG. 14 has a cannula 411 with adaptor ports 412, and the cannula 411 is connected to a patient's blood vessel 413 at a perpendicular angle (90"). In this way, a tip 414 of a stem of a plunger 415 within the cannula 411 can be slid far enough towards a proximal end of the cannula so that the tip 414 reaches a point where the proximal end of the cannula is level with the wall of the blood vessel, thereby preventing the filling of the patient's blood into the cavity or lumen 416 of the cannula. As a consequence, there is no dead space between the plunger tip 414 and the blood vessel 413 when the cannula 411 is connected to the patient's vessel at a perpendicular angle.

However, as shown in FIGS. 15 and 16, when a cannula 417 with an is connected to the patient's vessel at a non-perpendicular angle (say 30°), the regular cylindrical shape of the tip 414 of the plunger may create a protrusion 418 into the lumen of the vessel (see FIG. 15) or, if the tip 414 is retracted into the cannula to eliminate the protrusion, a dead space 419 is then created within the lumen of the cannula which will be filled with a small amount of blood (see FIG. 16). Both the protrusion 418 and the dead space 419 can cause or contribute to haemodynamic disturbances or turbulence within the patient's circulatory system that may result in thrombotic events. The amount of dead space or protrusion, when present, will vary according to the site of remote access, e.g. axillary, femoral, iliac, or jugular vessels.

Figure 17:
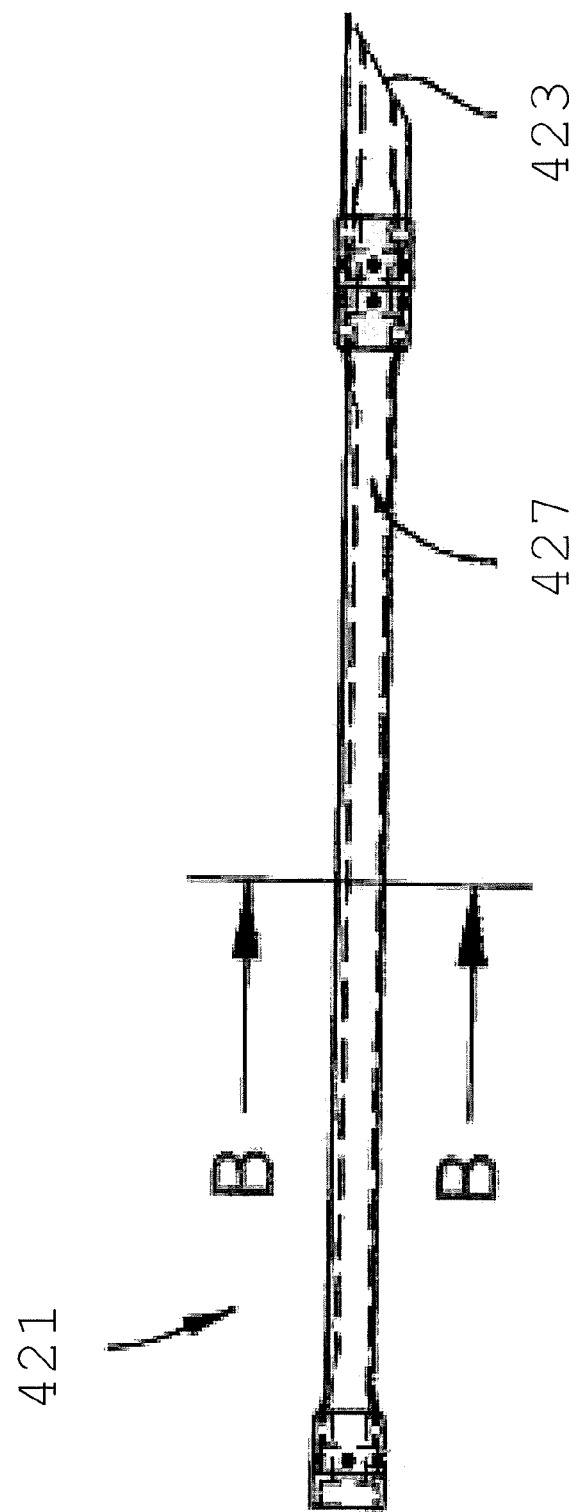
FIG. 17 is a side view of a cannula of a single lumen access device according to an embodiment of the present invention.
Figure 18:
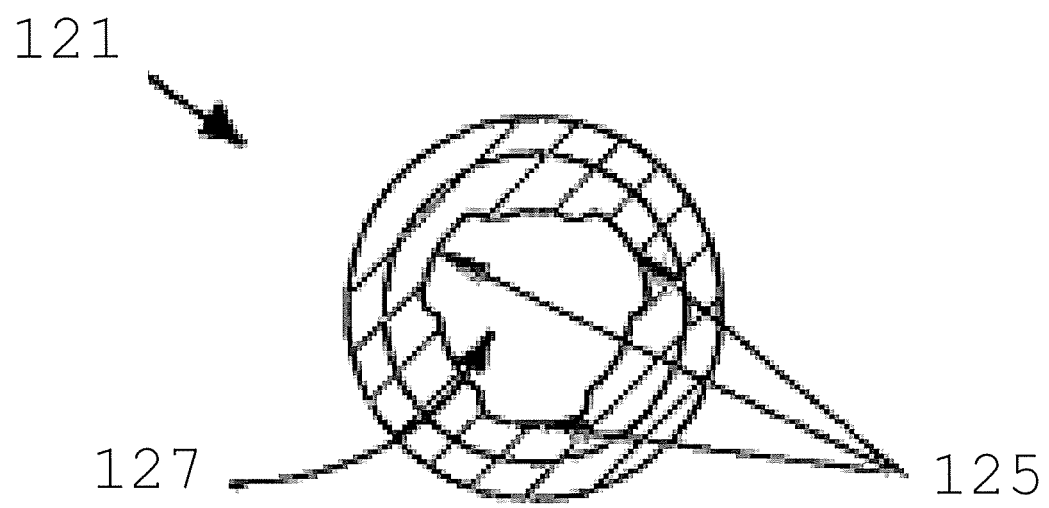
FIG. 18 is a sectional end view through B-B of the cannula of FIG. 17.
Figure 19:
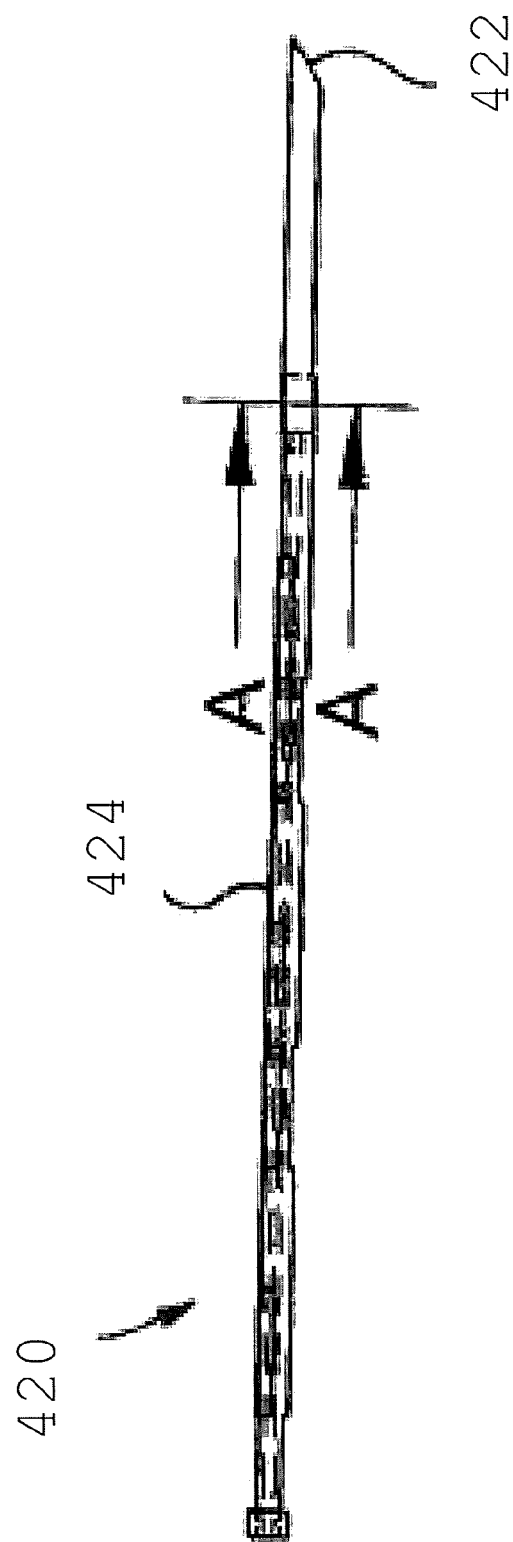
FIG. 19 is a side view of a plunger stem having a chamfered tip for use with the cannula shown in FIGS. 17 and 18 of the single lumen access device.
Figure 20:
FIG. 20 is a sectional end view through A-A of the plunger stem of FIG. 19.

The plunger 420 shown in FIGS. 19 and 20, which is for use with the cannula 421 of the present invention shown in FIGS. 17 and 18 to form the single lumen access device, avoids this problem by having a chamfered tip 422 or proximal end configured such that the angle made between the plane of the chamfer of the tip 422 and the longitudinal axis of the plunger 420 is identical to the angle made between the longitudinal axis of the cannula 421, through which the plunger stem travels, and the wall of the patient's vessel connected by the cannula 421. The plunger 420 acts to stop the flow of blood up the cannula 421. Blood flow up the cannula 421 can cause a thrombosis.

Figure 21:
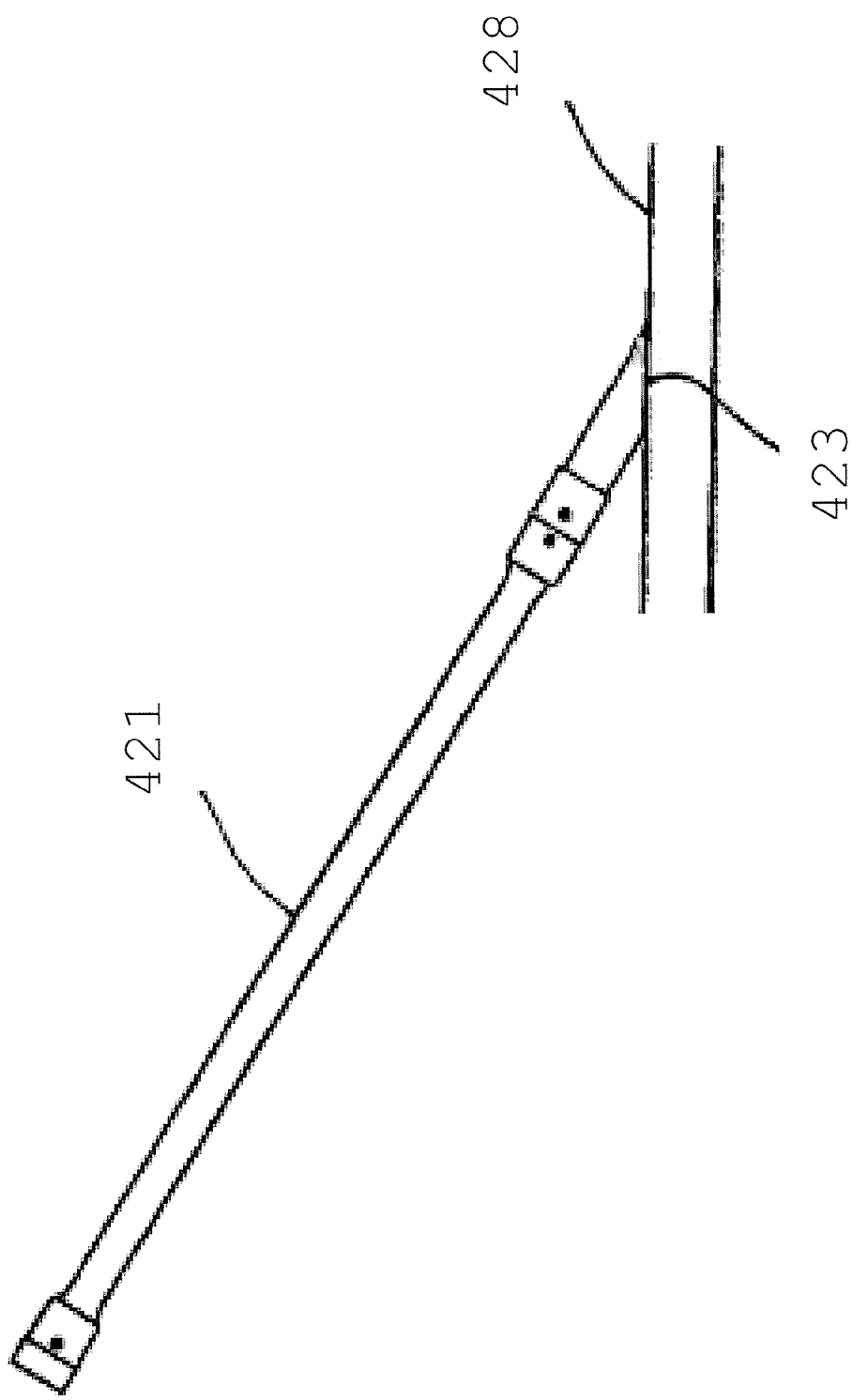
FIG. 21 is a side view of the single lumen access device formed of the cannula of FIGS. 17 and 18 and the plunger stem of FIGS. 19 and 20, with the single lumen access device being connected to a patient's blood vessel and not showing any resulting protrusion or dead space.

In one embodiment, the plunger 420 can include an internal lumen (not shown) running its entire length. The internal lumen can be plugged by a second plunger. The second plunger can removed to allow the provision of material through the internal lumen As shown in FIGS. 17 and 21, the cannula 421 has a proximal graft end 423 which has the same chamfered angle as that of the plunger tip 422 and a body portion 432 within which the plunger stem 424 sits. When the plunger stem 424 is slid down the body portion 432 of the cannula 421, the plane of the chamfer of the plunger tip 422 will be parallel with the patient's vessel wall 428, preventing dead space and thus reducing the likelihood of thrombotic events.

In one embodiment, the cannula 421 includes dacron cuffs along its length arranged to anchor the cannula 421 within the body.

As shown in the sectional end views of FIG. 18 and FIG. 20, the inner walls 425 of the body portion 432 of the cannula 421 are so contoured as to mateably correspond with the contour of the outer walls 426 of the plunger stem 420, thereby enabling the plunger stem 424 to, during its passage through the cannula 421, be guided in such a way that the chamfered surfaces of the proximal ends or tips 122, 123 of the plunger stem and cannula are correctly aligned. When the cannula 421 is connected to a patient's blood vessel at a non-perpendicular angle, and the plunger stem 424 is slid down the cavity 427 of the cannula 421, the alignment provided by the corresponding contoured walls 425, 426 mentioned above ensures that the chamfered surface of the plunger tip 422 will be parallel and in line with the vessel wall 428 so as to prevent any dead space within the lumen 427 of the cannula 421 or any protrusion into the vessel lumen. Haemodynamic disturbances that could result in thrombotic events will be prevented by this feature; and this will allow the access device to be used for a longer implant period without reducing its safety.

Figure 22:
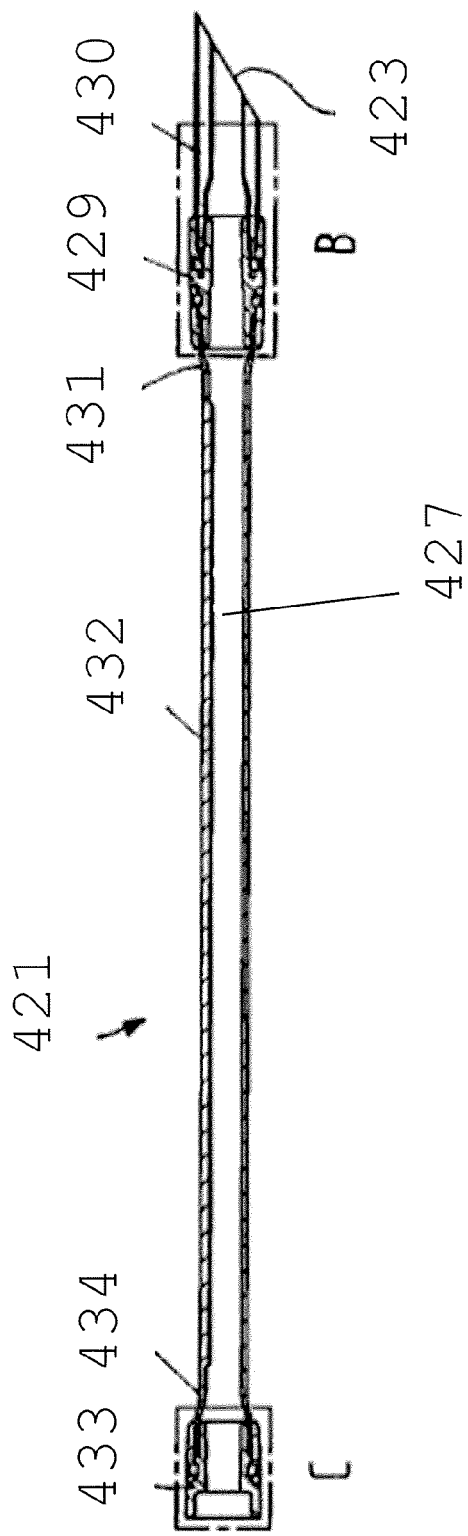
FIG. 22 is a sectional side view (longitudinally) of the cannula of FIG. 17.
Figure 23:
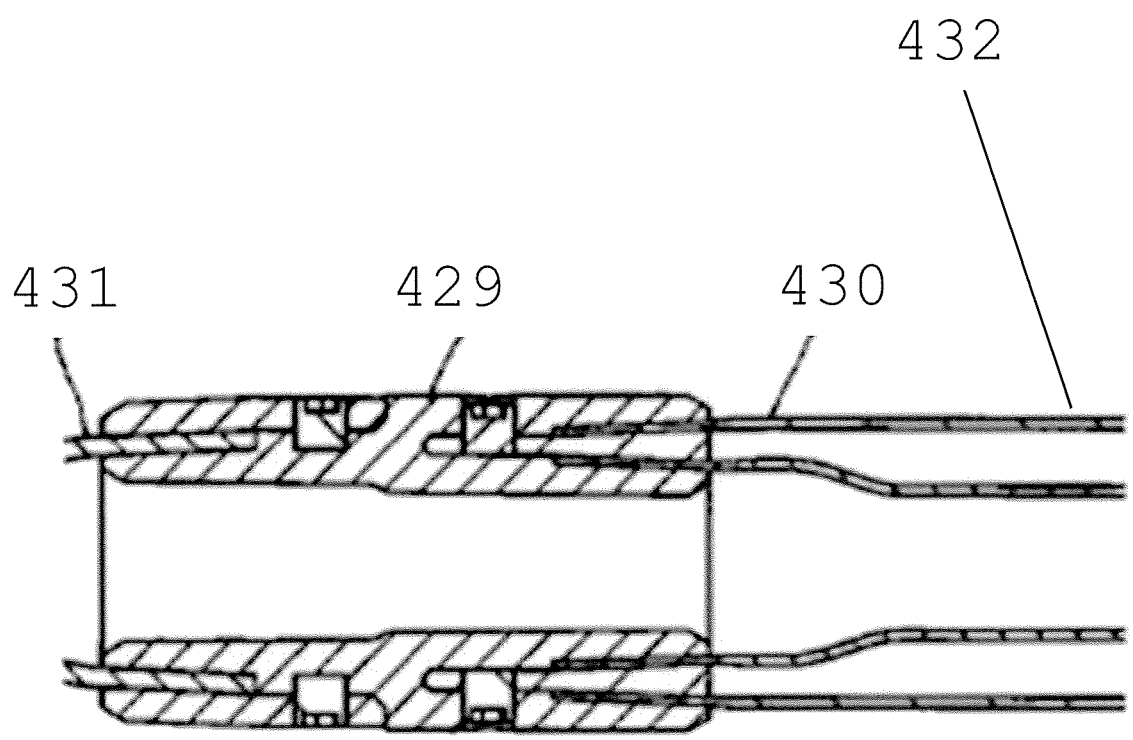
FIG. 23 is an enlarged view of the sectioned part B of the cannula as shown in FIG. 22.
Figure 24:
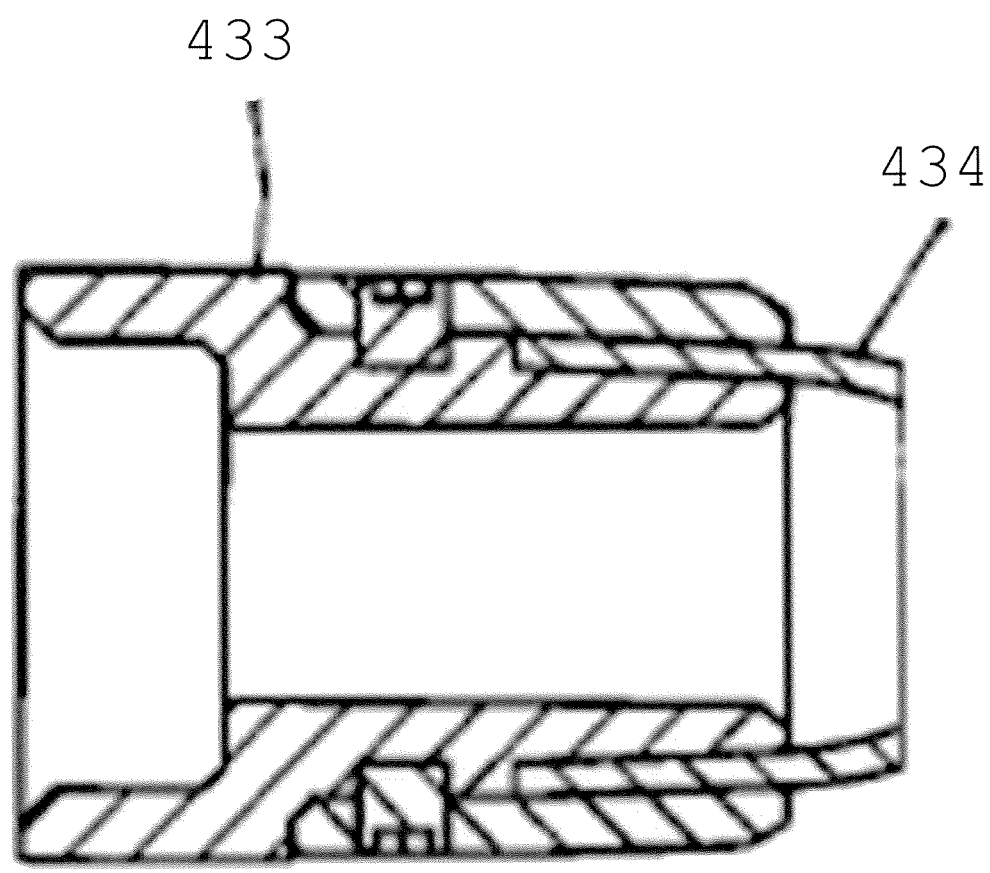
FIG. 24 is an enlarged view of the sectioned part C of the cannula as shown in FIG. 22.

FIG. 22 shows a sectional view longitudinally of the cannula 421; whilst FIG. 23 shows in sectional detail how a connector assembly 429 interconnects a proximal graft end portion 430 of the cannula 421 to an adjacent end portion 431 of a main body 432 of the cannula 421. FIG. 24 shows in sectional detail how a connector assembly 433 is connected to a distal end portion 434 of the main body 432 of the cannula 421. The connector assembly 433 enables connection to a medical supply device such as a multiport adaptor; a pump, a drug supply, a radiation supply or otherwise.

Figure 21A:
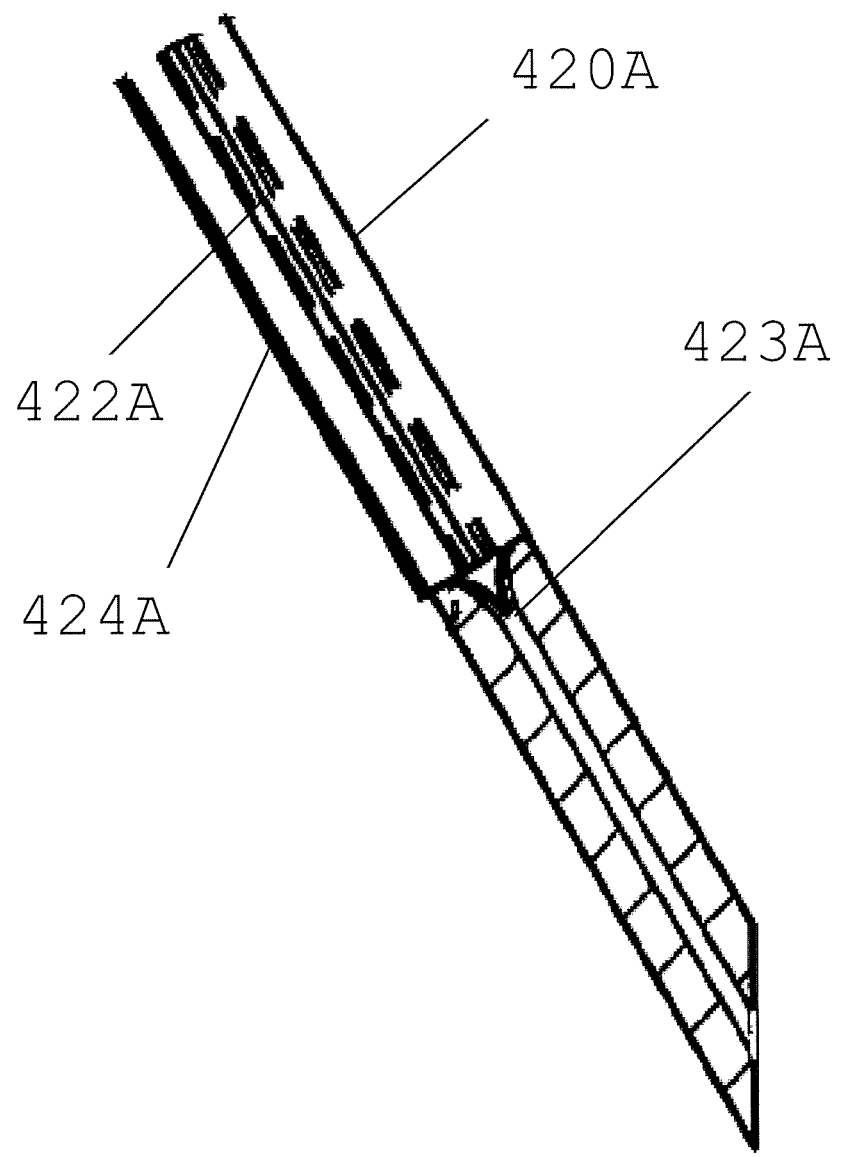
FIG. 21A is a side view of an alternative cannula to the cannula of FIG. 17.

With reference to FIG. 21A; an alternative to the use of cannula 421 with a plunger stem 424 is shown. Instead second plunger stem 420A is used to stop the flow of blood up the lumen of the cannula 421 is used. The second plunger stem 420A includes passageway 422A along its length. The passageway 422A includes a one way valve 423A to allow injection of material into the cannula 421 whilst stopping fluid and particulates flowing into the passageway 422A from the cannula 421.

The blood vessel access device with a chamfered end of FIGS. 14 to 24 provides an access device for the catheters 22 and balloons 24 for the isolation and therapeutic treatment of a region of the body or organ ad discussed above.

Broadly, with reference to FIGS. 25 to 30 an embodiment of the present invention relates to a multiport adaptor device for facilitating the insertion of multiple catheters into a single cannula lumen.

Figure 25:
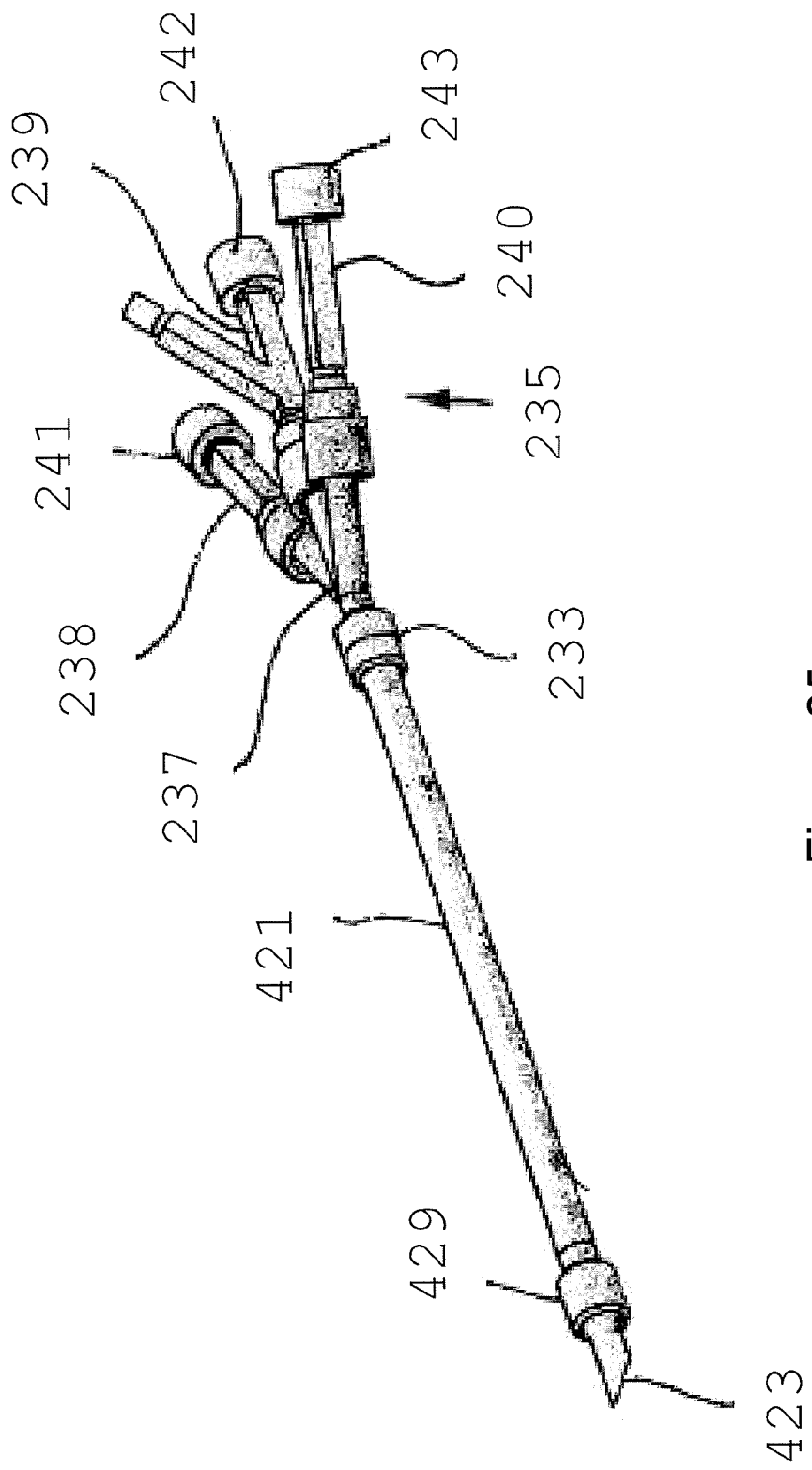
FIG. 25 is a perspective view of a multiport adaptor according to an embodiment of the present invention connected, for use, with a cannula of a single lumen access device.
Figure 26:
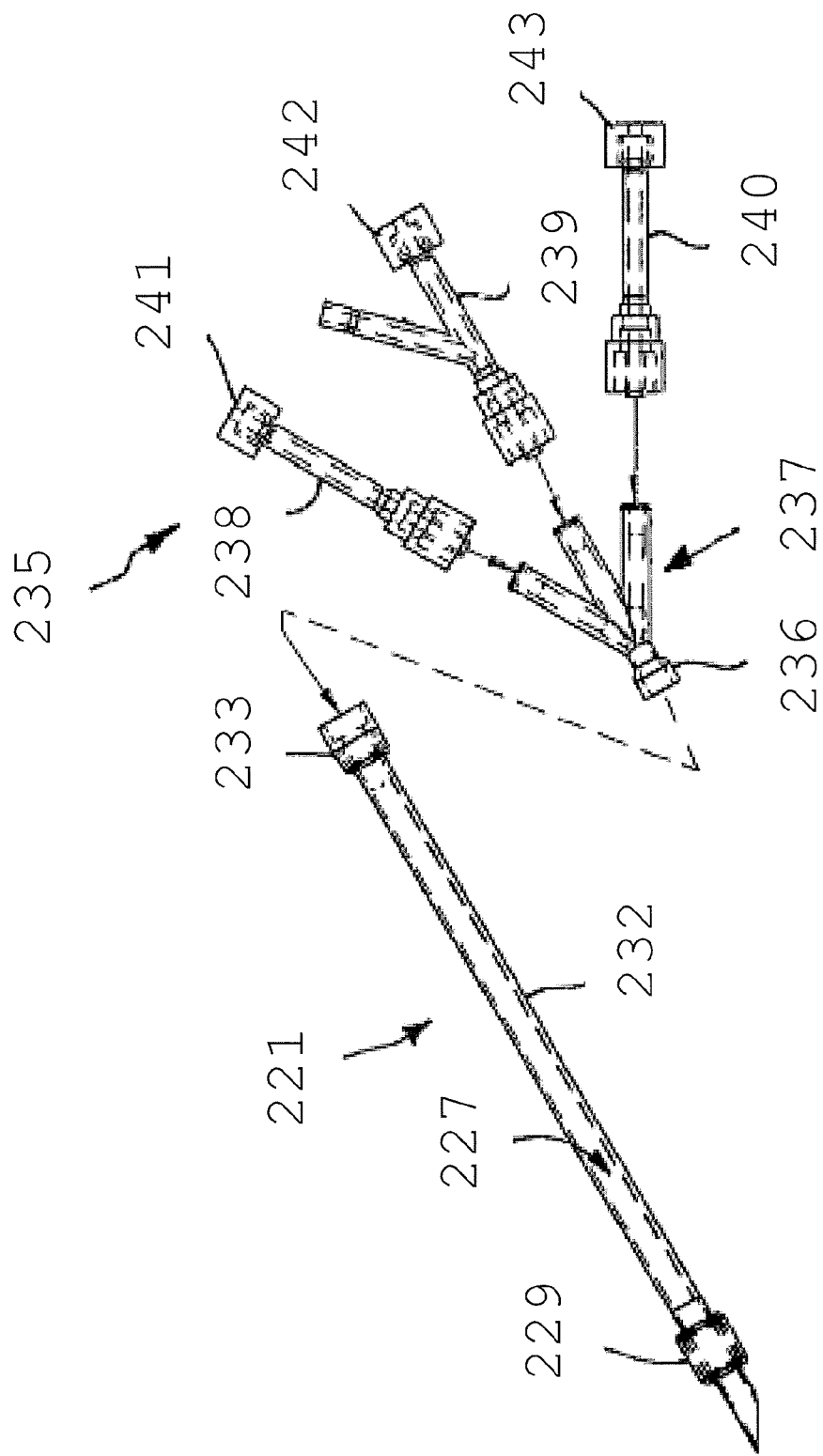
FIG. 26 is an exploded view of the multiport adaptor shown in FIG. 25 alongside the cannula.
Figure 27:
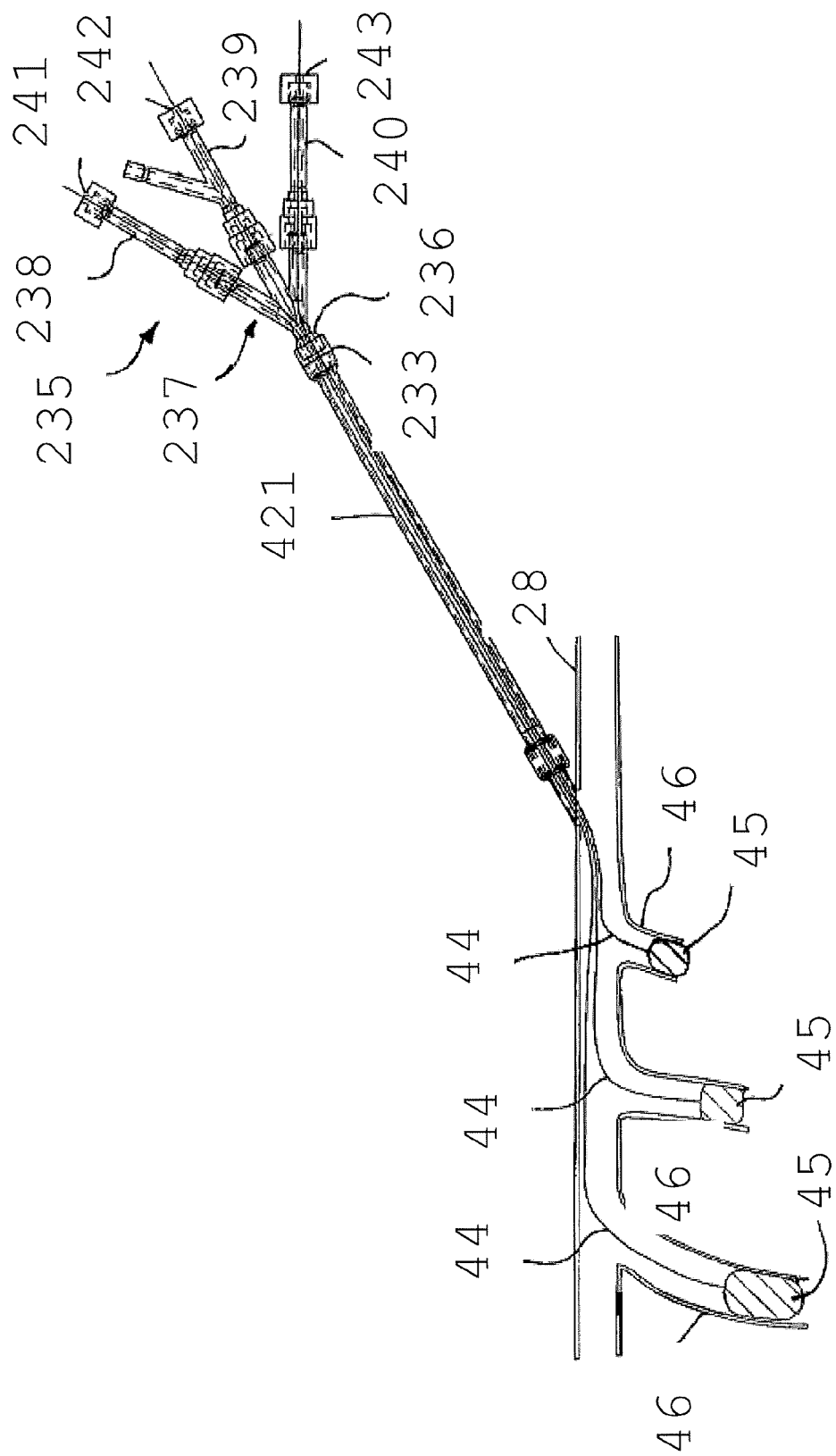
FIG. 27 is a side view of the interconnected multiport adaptor and cannula of FIG. 25 shown connected to a patient's circulatory system and showing an occlusion balloon positioning arrangement of three separate balloon catheter systems which all pass through the lumen of the cannula into the circulatory system to control vascular flow to or from an organ.

The multiport adapter 235 shown in FIGS. 25 to 27 has a unitary end port 236 that is adapted to be connected onto the connector assembly 233 at the distal end portion 234 of the cannula 421 of FIGS. 17 to 24. The adapter 235 has a branched portion 237 which diverges into three tubes, to each of which is releasably connected an item of external tubing 238, 239, 240 having respective outer ports 241, 242, 243 that are designed to fit other medical devices with a male luer lock medical fitting of the type described in U.S. Pat. No. 5,047,021. The skilled addressee will recognise that alternative connection means may be used to be used to connect the outer ports 241,242, 243 to other medical devices. Such medical devices may be haemostasis valves (see U.S. Pat. No. 5,195,980; EP 0875262; U.S. Pat. No. 6,22,1057), medical three-way stopcocks (see U.S. Pat. No. 7,914,495), and syringes (see U.S. Pat. No. 8,652,109). The adapter 235 can also receive catheters 44 and balloons 45 of three balloon catheter systems which all pass through the lumen of the cannula 421 and which are used in vascular isolation systems and to allow improved and enhanced communication with the patient's circulatory system.

Figure 25A:
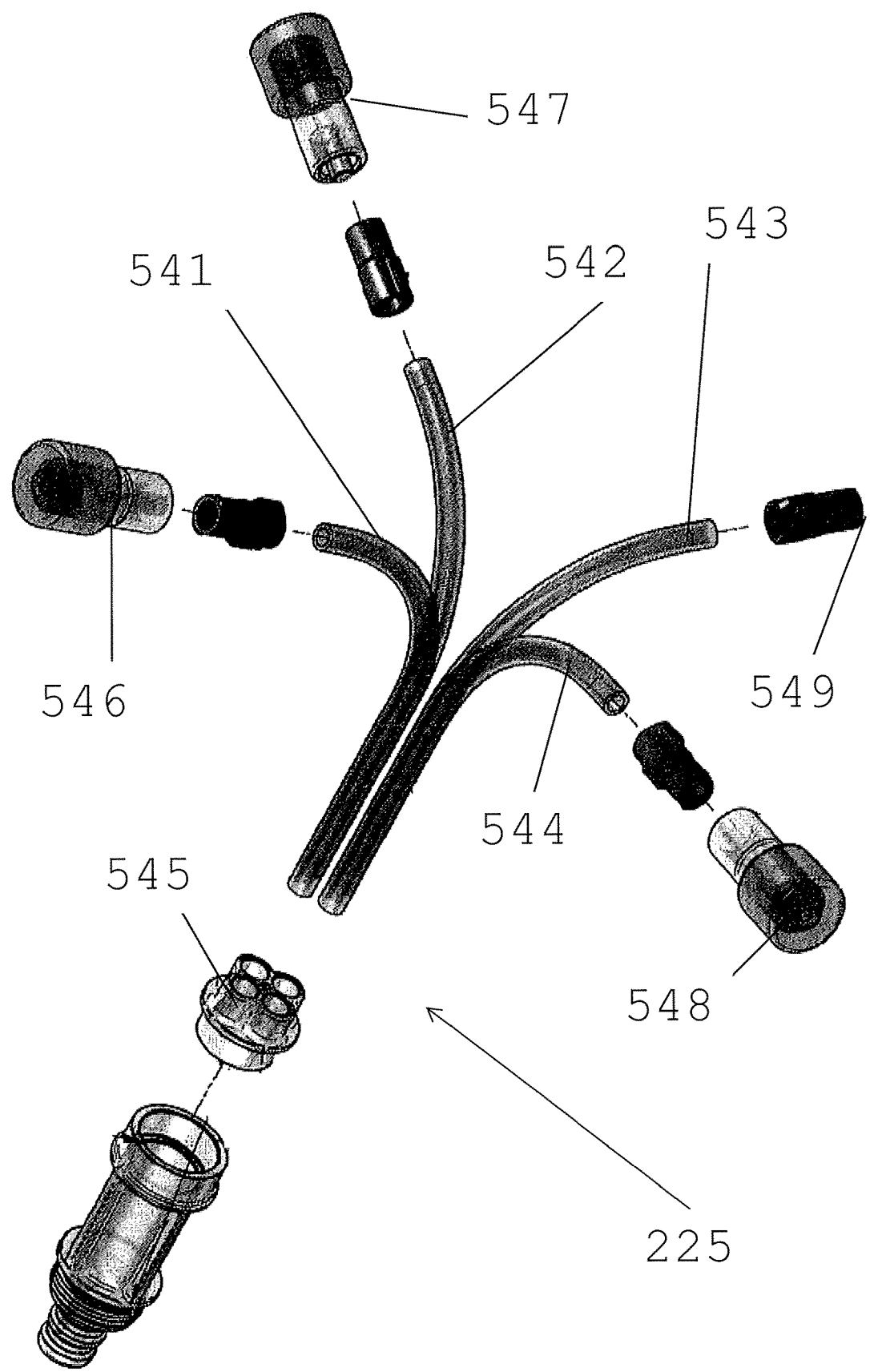
FIG. 25A is a perspective view of a multiport adaptor according to an embodiment of the present invention.

As shown in the embodiment of FIG. 25A a multiport adaptor 225 is shown. The multiport adaptor 225 includes four tubes 541, 542, 543, 543 that are flexible and serve to act as a guide for the placement of catheters placed through the different tubes. The flexible tubes 541, 542, 543, 544 allow independent steerage for the placement of the catheters through feeder connection port 545 where moving one flexible tube only affects one catheter without impacting other catheters. The tubes 541, 542, 543, 544 have their distal ends connected to outer ports 546, 547, 548, 549.

In an alternative embodiment multiport adaptor includes more than three tubes. In yet a further alternative embodiment, the plurality of tubes of the multiport adaptor are located within a unitary body to fix the location of the tubes with respect to each other.

The skilled addressee will recognise that alternative connection mechanism to a male luer lock can be used and still fall within the scope of the present invention.

The vascular isolation systems introduced into the patient's circulatory system are then used to control or even occlude the blood flow through the vessels 246 to and/or from an organ or a segment thereon. The adaptor 235 serves as an extracorporeal component of the access device. Where a plurality of smaller cannulas 44 are fed through the multiport adaptor 235 into the cannula 221 each of the smaller cannulas 44 can be directed to different positions to occlude or control the blood flow.

Figure 28:
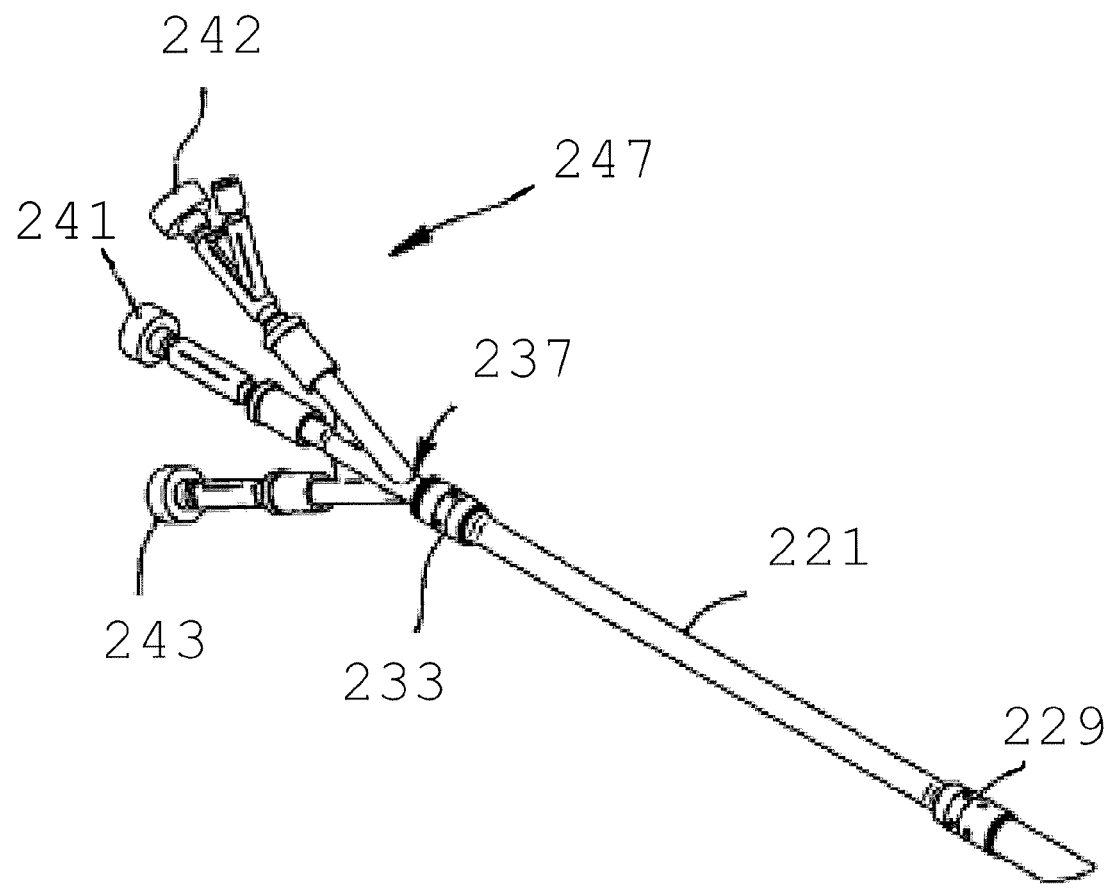
FIG. 28 is a perspective view of a multiport adaptor according to another embodiment of the second invention connected, for use, with an implantable cannula of a single lumen access device.
Figure 29:
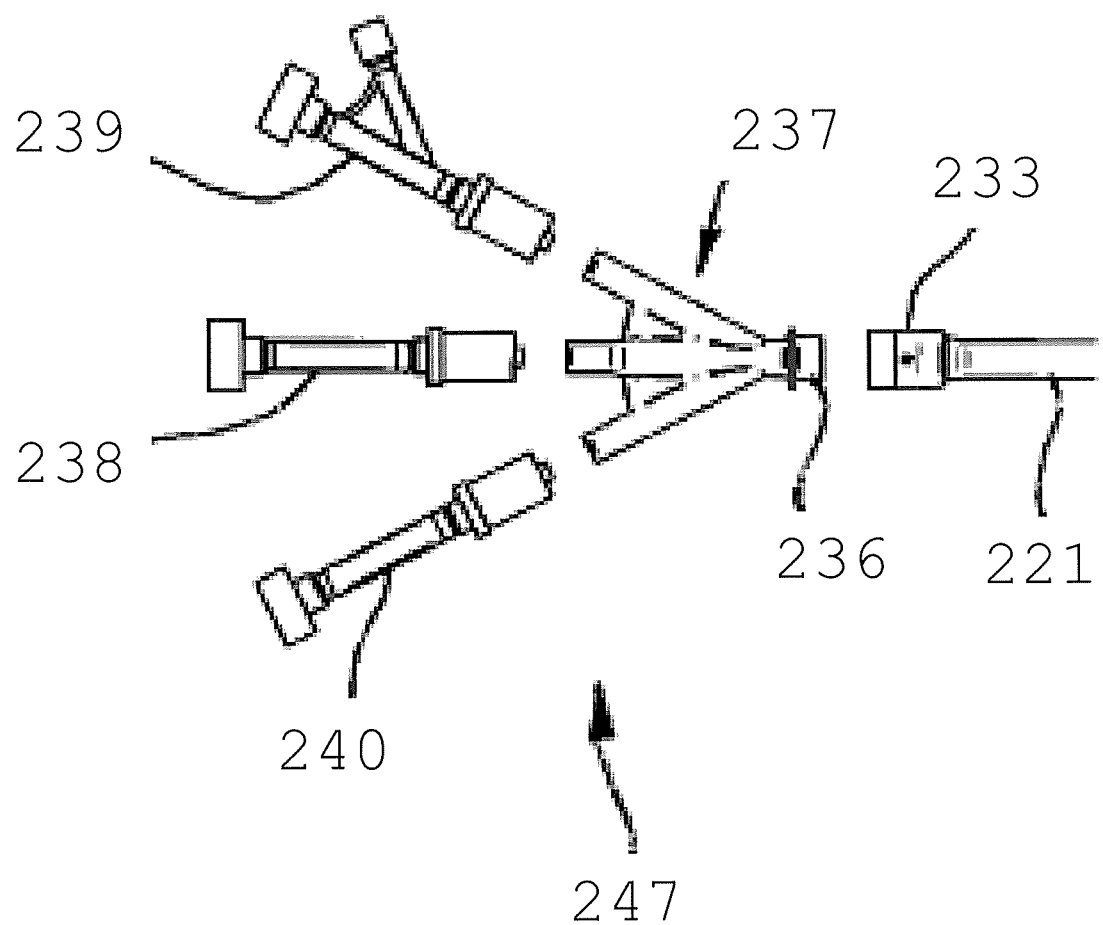
FIG. 29 is an exploded view of the multiport adaptor shown in FIG. 28 alongside a distal end of the implantable cannula.
Figure 30:
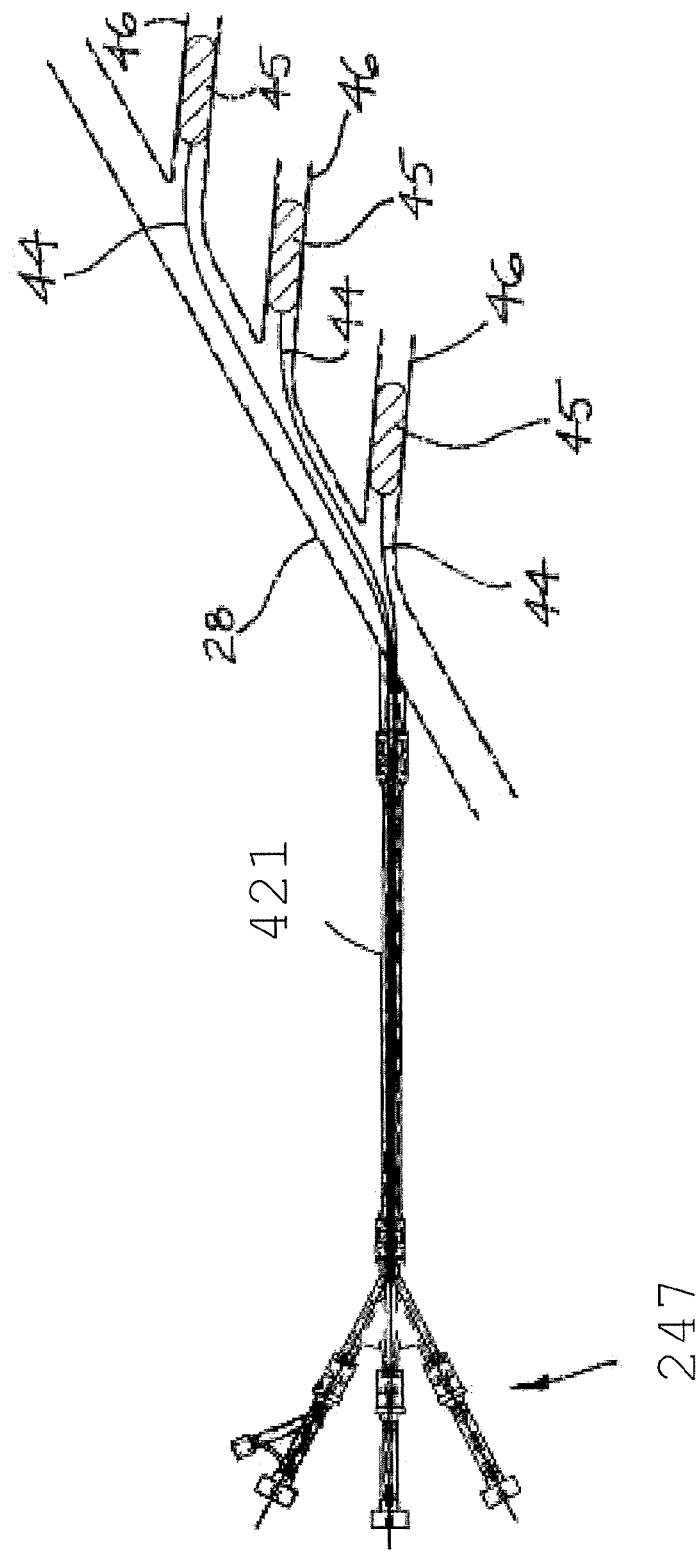
FIG. 30 is a side view of the interconnected multiport adaptor and cannula of FIG. 28 shown connected to a patient's circulatory system and showing an occlusion balloon positioning arrangement of three separate balloon catheter systems which all pass through the lumen of the cannula into the circulatory system to provide vascular isolation of an organ.

FIGS. 28 to 30 show the implantable cannula 421 of FIGS. 17 to 24 connected at its distal end to the unitary end port 236 of a multiport adaptor 247 which is similar in structure and function to that shown in FIGS. 25 to 27. FIG. 30 shows the cannula 421 connected directly to the wall 228 of a patient's artery or vein. The multiport adaptor 247 also diverges to form a plurality of outer ports provided with ISO standard fluid/gas tight connections suitable for vascular applications. Three catheters 244 and balloons 245 all pass through the lumen of the implantable cannula 421 via the outer ports of the multiport adaptor 247, and the balloons 245 occlude blood flow through the vessels 246.

The function of the multiport adaptor 235, 247 in facilitating the insertion of additional devices through the lumen of the implantable cannula 421 allows for multiple endovascular devices, such as catheters and balloons (hereinafter referred to as "balloon catheters", to be introduced simultaneously into the patient's vasculature via the implantable cannula. These endovascular devices can then be used simultaneously to administer treatments in a variety of ways.

An example of a possible treatment involves the vascular isolation of organs or anatomical regions of the human body, including but not limited to the liver, pancreas or pelvic organs. In this example, multiple cannulation systems employing balloons and catheters are inserted into the patient's vasculature using the implantable cannula 421 and multiport adaptor 235, 247 and subsequently positioned in the arteries supplying blood to the target area or lesion. The balloons of these balloon catheter systems are then inflated, cutting off or occluding the arterial inflow to the target area and establishing an isolated zone of significantly reduced blood inflow. This isolated zone allows for infusion of therapeutic agents into the target area whilst minimizing systemic exposure. Vascular isolation may be further enhanced by using a separate access device to locate additional balloon catheter systems in the veins so as to occlude venous outflow from the target area or lesion, or by using positive end expiratory pressure (PEEP).

With reference to FIGS. 31 to 35, external vascular fistula devices 300, 315, 320 according to an embodiment of the present invention are shown. These fistula devices 300, 315, 320 allow repeated sterile access to the arterial and venous side of the circulation without interruption of the flow of blood through the fistula devices 300, 315, 320. In addition, the connector can be removed and replaced following arterial and venous control. The device allows sampling of blood without separate venous puncture. This capability improves the quality of life of cancer patients on chemotherapy who require a great deal of testing to particularly look at the haematological effects of the chemotherapy. The device allows catheter insertion for continuous remote intra-arterial or intravenous infusion for delivery of chemotherapy, stem cells or nano particles or antibiotics. The system may also have a catheter loop within itself for example for real time recognition of cell type. A catheter is inserted into the arterial side of the fistula devices 300, 315, 320 and this traverses a device which immediately recognises cell type in real time and then delivers the blood back into the venous system without interruption of fistula flow. A similar system is extraction via the venous part of the fistula devices 300, 315, 320 and re-insertion via a pump into the arterial system; this is known as remote closed loop recirculation. This is appropriate in some forms of chemotherapy, particularly if detoxification is required. The device is also appropriate for repetitive diagnostic angiography by insertion of a catheter into the arterial venous side as required. The device construction addresses safety issues with essentially minimal chance of spontaneous dislocation and tampering.

In fistulae, in the past the venous system may undergo intimal hyperplasia with the gradual reduction of flow and eventual inclusion. This may or may not be treatable with appropriate angioplasty or operation. Under these circumstances the fistula device 300, 315, 320 is compatible with both of the arterial and venous vascular tube and therefore allows the access to be continued by plugging the tube with a plunger i.e. if necessary the access device can be removed and replaced by plungers in either or both access tubes.

Alternatively, a previous single intra-arterial device can be converted into a fistula device 300, 315, 320 if the access to the other side of the circulation is required.

Figure 31:
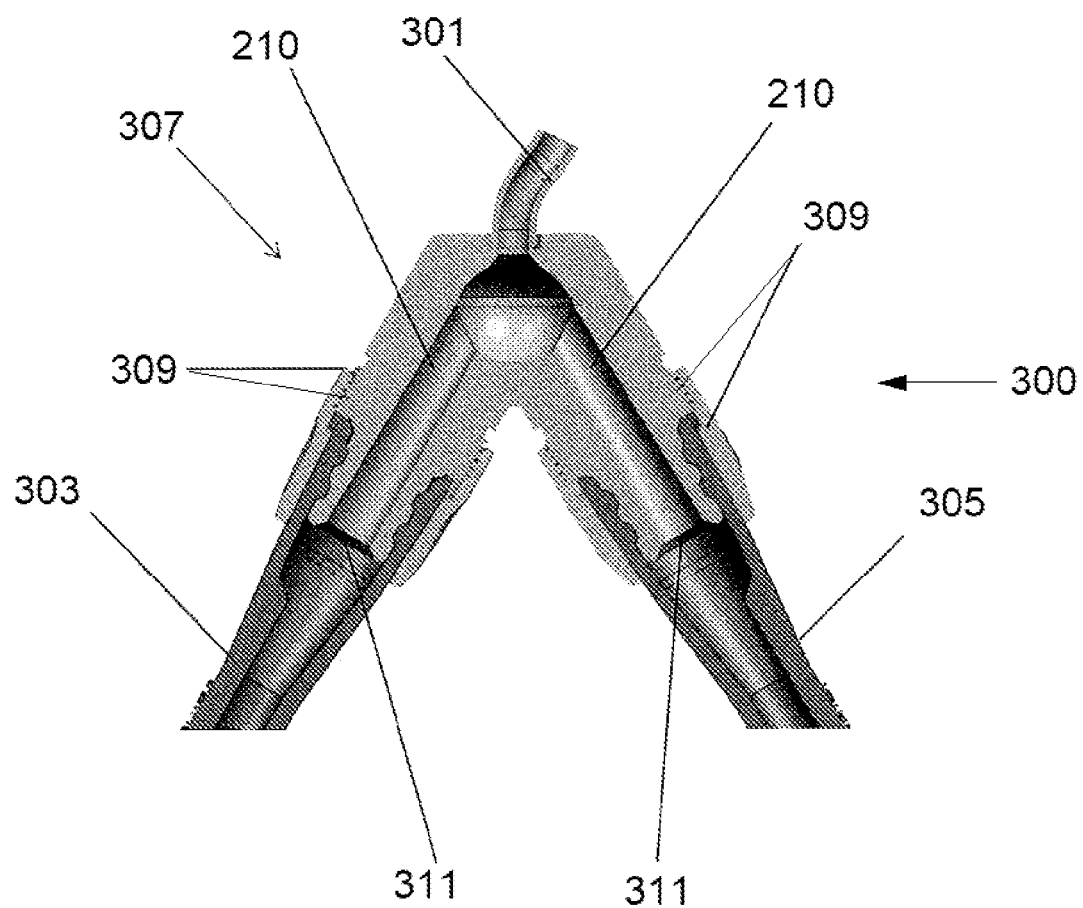
FIG. 31 is a side view of an external fistula device according to an embodiment of the present invention.

Referring to FIG. 31, an external fistula device 300 is shown. The external fistula device 301 includes a bridging device 307 designed to connect to arterial cannula 303 and venous cannula 305. The bridging device 307 acts to provide a passageway 310 between the arterial cannula 303 and venous cannula 305 to allow blood to flow through. The bridging device 307 includes engagement means 309 to fix the bridging device 307 to the arterial and venous cannulas 303, 305. The engagement means 309 can be in the form of a screw thread, a clip, a snap fit or otherwise and understood by the skilled addressee. The passageway 210 of the bridging device 307 sealingly engages with the passageways of the arterial and venous cannulas 303, 305 at engagement point 311. Engagement point 311 includes a seal to stop leakage of blood passing into or from the bridging device.

An access portal 301 is located on the bridging device 307 to provide access to the arterial and venous cannulas 303, 305. The access portal 301 feeds directly into the passageway 210 allowing catheters to be fed into either or both of the arterial side or venous side of the fistula connection. This arrangement allows for repeated catheterisation through access portal without needing to compromise the connection between the arterial and venous cannulas.

Figure 32:
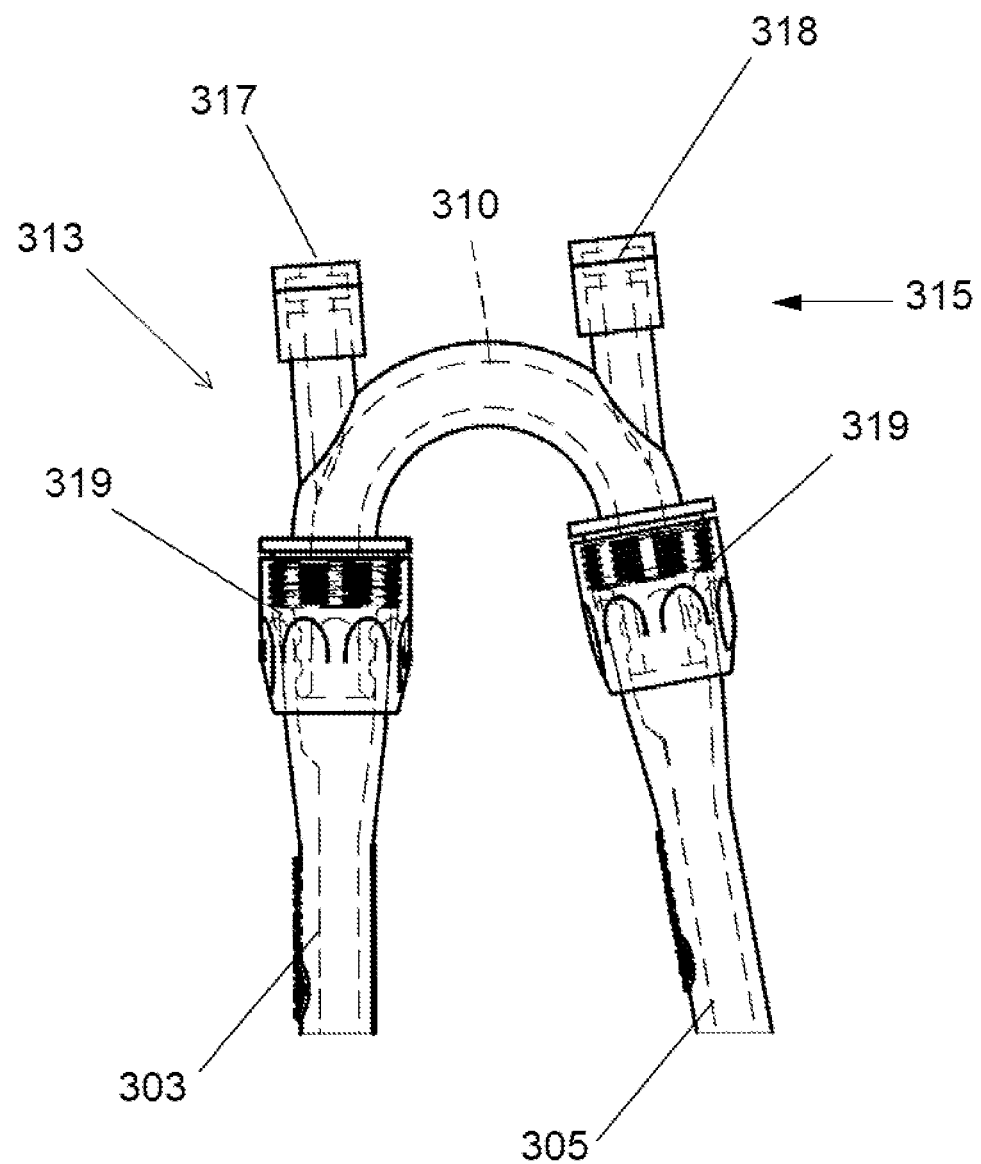
FIG. 32 is a side view of an external fistula device according to an embodiment of the present invention.

Referring to FIG. 32, an alternative external fistula device 315 is shown connected to arterial cannula 303 and venous cannula 305. As with the embodiment of FIG. 31, a bridging device 313 with passageway 310 is used to connect the arterial and venous cannulas 303,305 together. Connection devices 319 sealingly fix the bridging device 313 to the arterial and venous cannulas 303, 305. The bridging device includes both arterial side access portal 317 and a venous side access portal 318. Arterial access portal 317 is used to insert catheters through the arterial cannula 303 into an artery. Venous access portal 318 is used to insert a catheter through the venous cannula 305 into a vein. Seals at the top of arterial access portal 317 and venous access portal 318 allow repeated catheterisation through the bridging device without needing to puncture arteries or veins.

Figure 33:
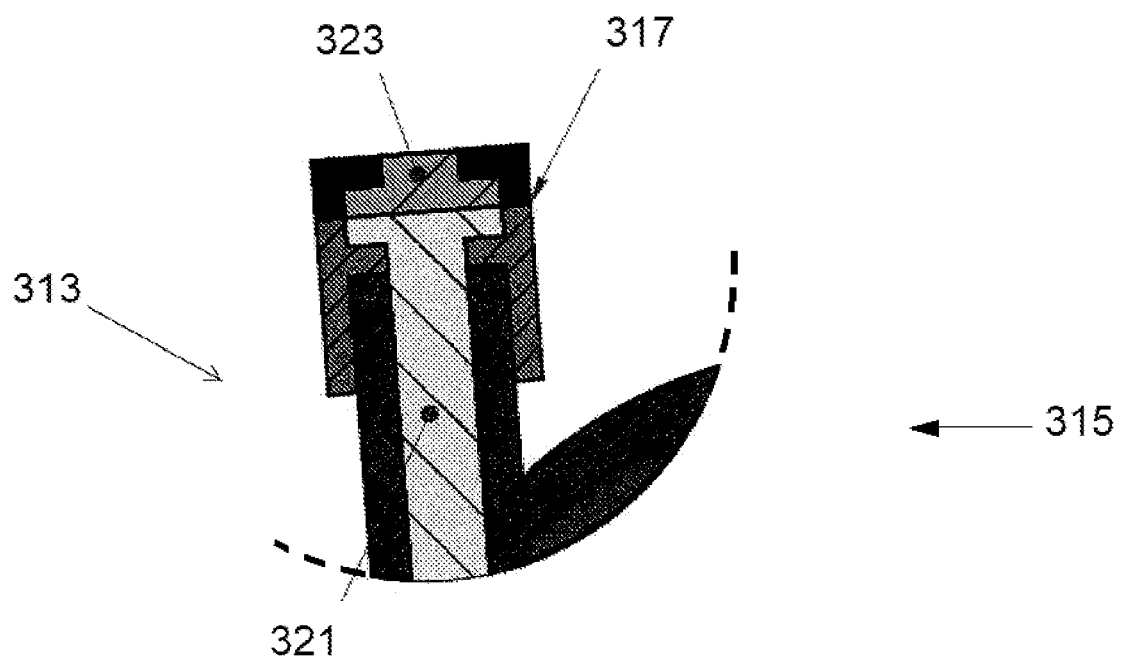
FIG. 33 is a side view of a port used in the external fistula device of FIG. 32.

FIG. 33 illustrates the arterial access portal 317 of FIG. 32. A catheter is inserted through seal 323 through passageway 321 into arterial cannula 303.

Figure 34:
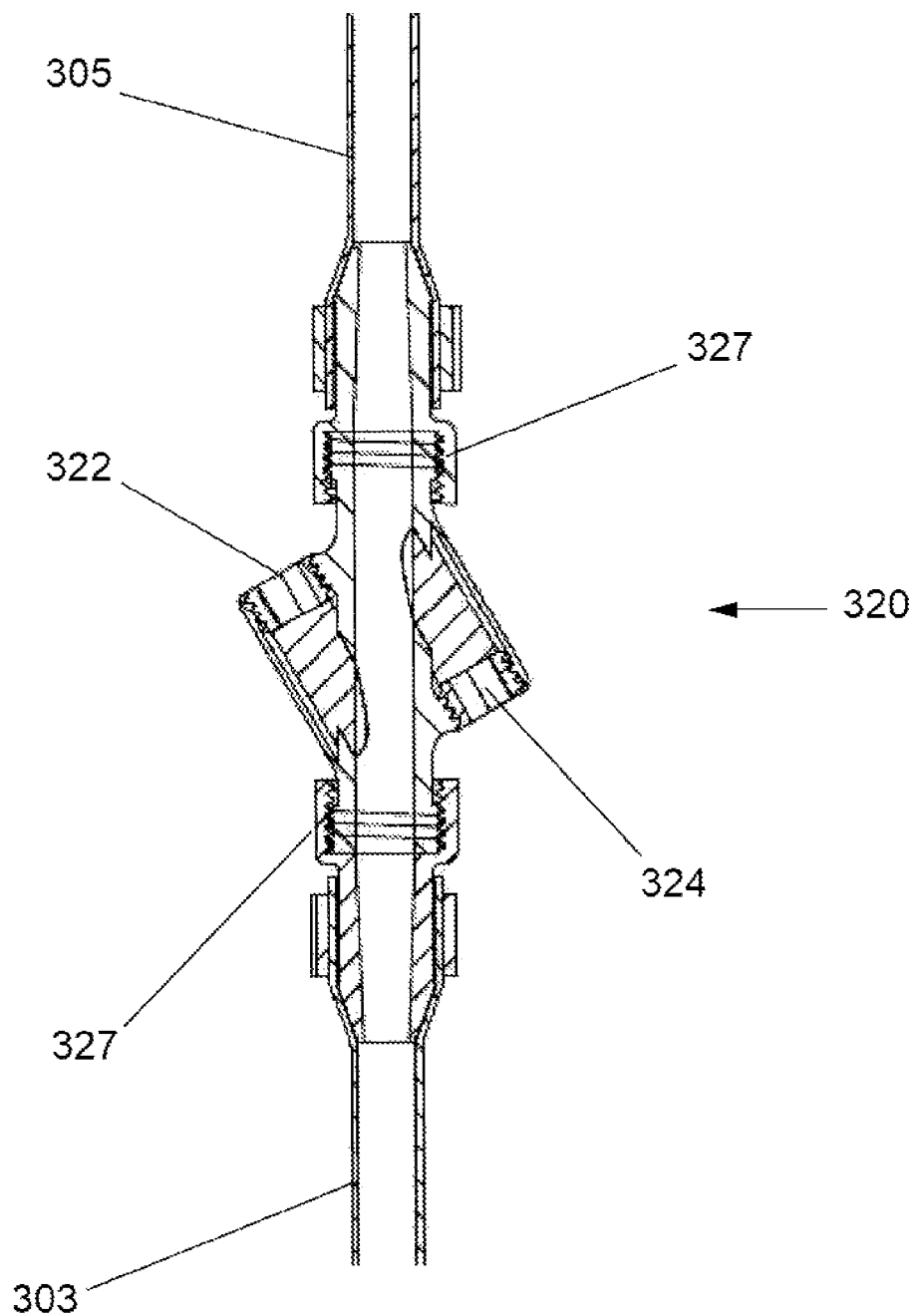
FIG. 34 is a side view of an external fistula connector device according to an embodiment of the present invention.

FIG. 34 illustrates an alternative external fistula device 320. As with the previous embodiments connection means 327 fix the external fistula device 320 to the arterial and venous cannulas 303, 305. Arterial access portal 322 includes a seal and is arranged to receive a catheter for insertion to an artery. Venous access portal 324 includes a seal and is arranged to receive a catheter for insertion to a vein. The connection means can be in the form of a threaded screw mean, a clip, a clamp or otherwise as understood by the skilled addressee. The arterial and venous access portals 322, 324 are arranged for repeated use so that catheters can be easily inserted and removed. In one embodiment the T arterial and venous access portals 322, 324 include a pierceable membrane.

In one embodiment the external fistula device is flexible.

Figure 35:
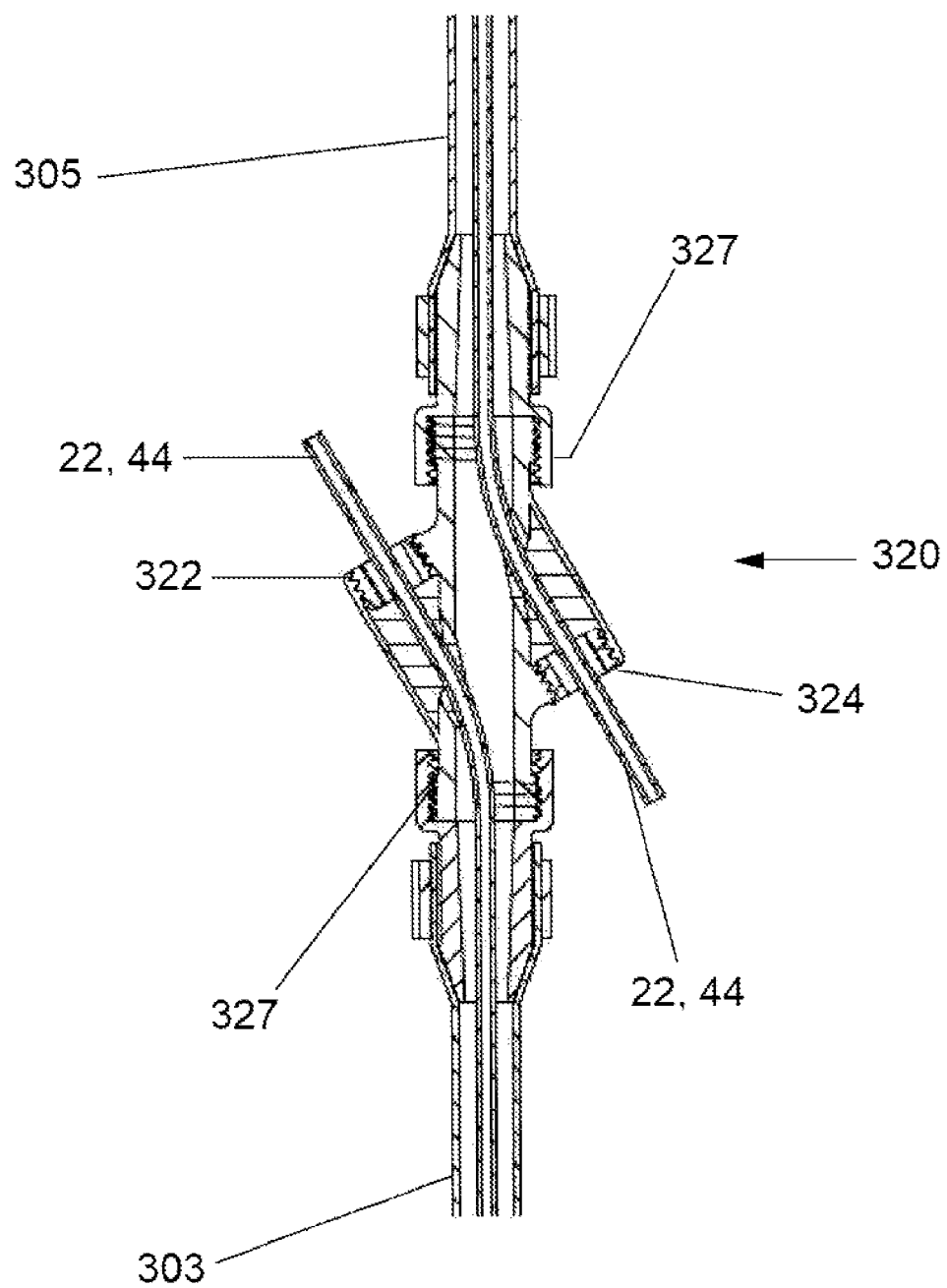
FIG. 35 is a side view of the external fistula connector device of FIG. 34 cannulated.

With reference to FIG. 35, the alternative external fistula device 320 of FIG. 34 is shown with catheters inserted into an artery and vein via the arterial and venous access portals 322, 324.

Figure 36:
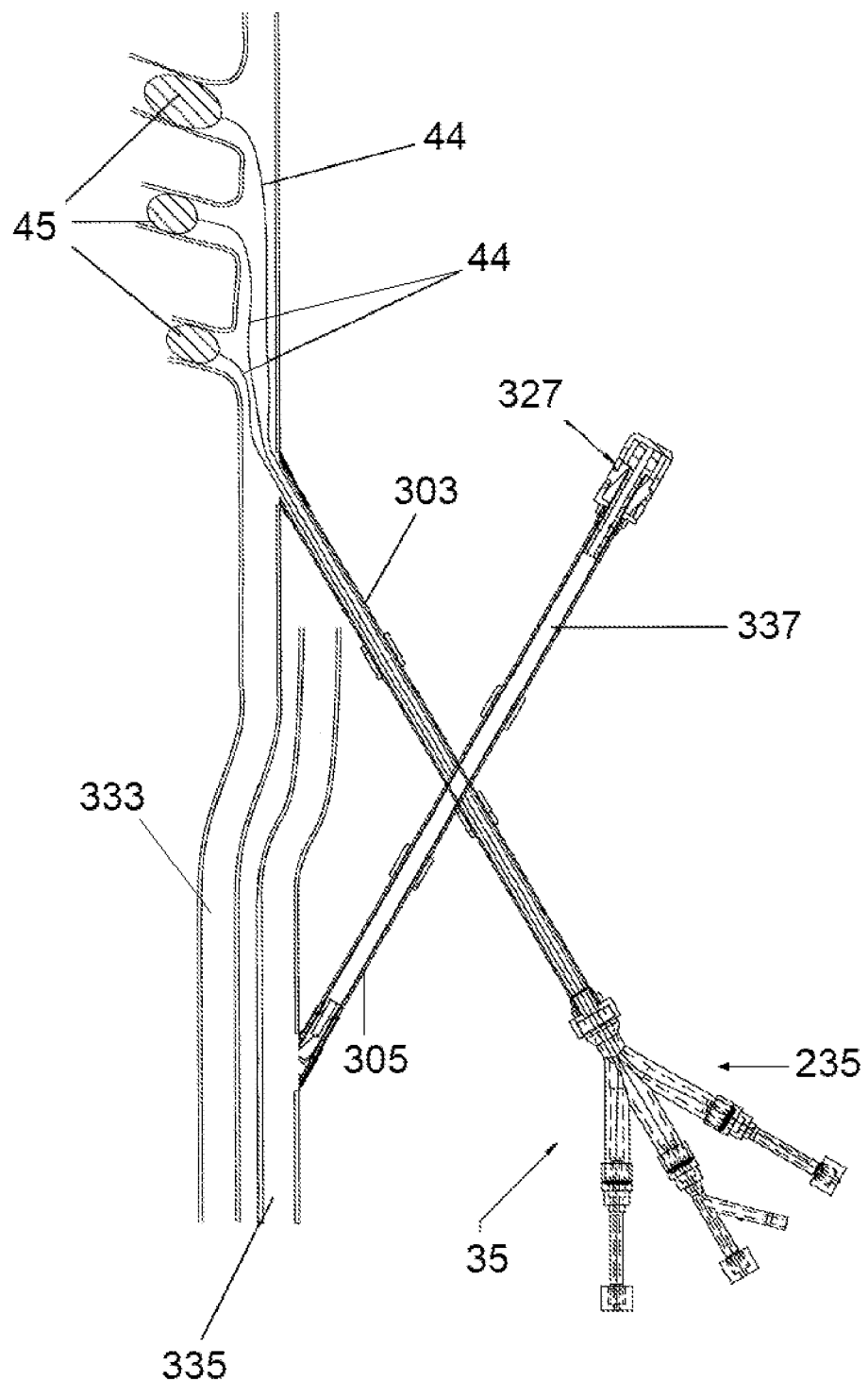
FIG. 36 is a side view of a multiport catheter connection and plunger according to an embodiment of the present invention.

FIG. 36 illustrates a scenario where the alternative external fistula device 320 has been removed from the connection between arterial and venous cannulas 303, 305 leading into artery 333 and vein 335. A plunger 337 is placed through connection means 327 into venous cannula 305 to plug the venous blood. Multiport adaptor 35 is connected to arterial cannula 303 to allow insertion of catheters 44 and balloons 45. This allows for the occlusion of arteries and the isolation of organs to use the method discussed above for therapeutic treatment.

Figure 37:
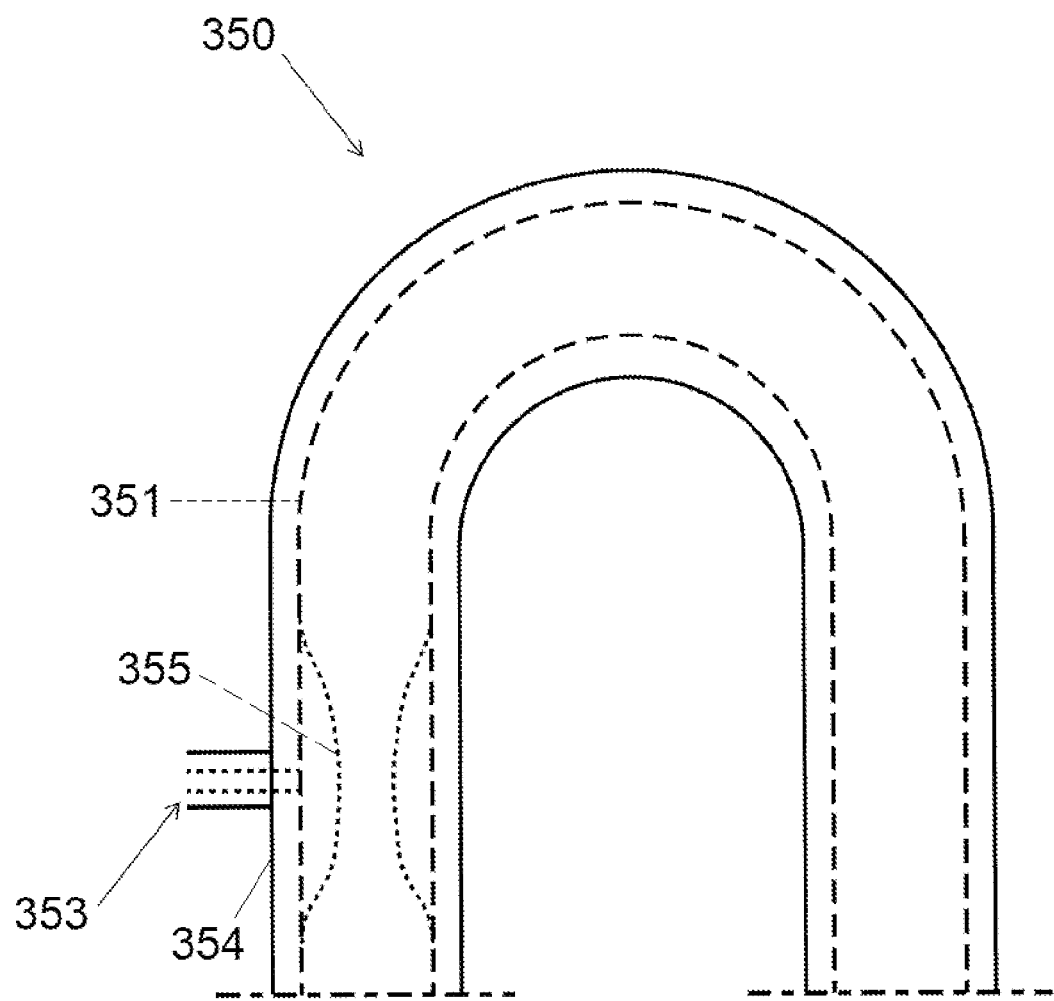
FIG. 37 is a side view of an external fistula device according to the present invention.
Figure 38:
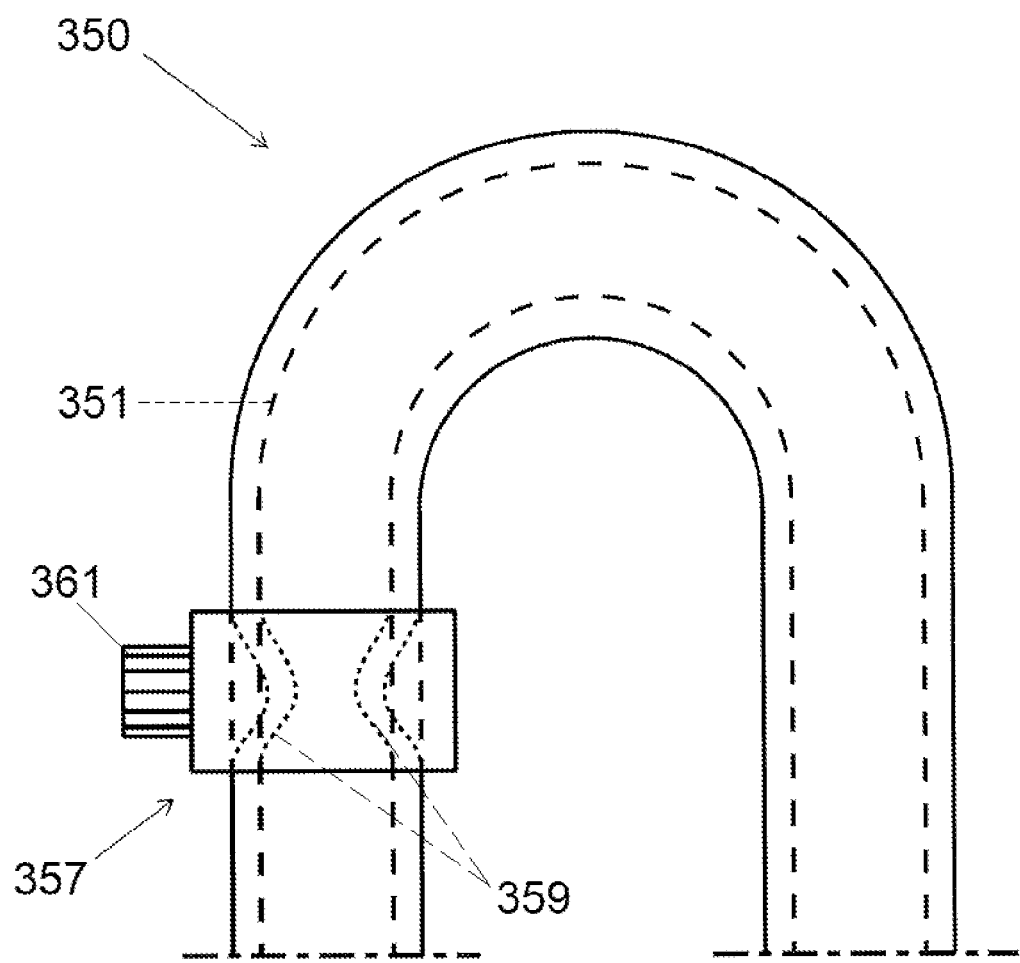
FIG. 38 is a side view of an external fistula device according to the present invention.

With reference to FIGS. 37 and 38, an external fistula device 350 is illustrated. The external fistula device includes an internal tube 351.

In the embodiment of FIG. 37, a first constriction device 353 engages the outer housing 354 of the external fistula device 350. A constriction control element 355 passes into the external fistula device and engages the internal tube 351. The constriction device applies force to the inner tube and constricts a reduced diameter portion 356 of the internal tube 351. The constriction device 353 can apply side to side constriction of the internal tube 351. Alternatively, the constriction device 353 can apply circumferential constriction to the internal tube. The constriction device 353 can apply with a screw, hydraulic, pneumatic means or otherwise as understood by the skilled addressee.

In the embodiment of FIG. 38 similar elements as present in FIG. 38 have been given the same numbering. A second constriction device 357 is placed around the outer housing 354 of the external fistula device 350. The second constriction device 357 constricts both the outer housing 354 and the internal tube 351 at constricted region 359 of the external fistula device 350. The constriction can be either side to side or circumferential and is controlled by control element 361 which is a screw, hydraulic, pneumatic means or otherwise as understood by the skilled addressee.

For both the embodiments of FIGS. 38 and 39, the constricted internal tube 351 allows control of the flow rate of fluid through the fistula.

Alterations and Modifications to the Embodiments

Various additions, modifications and substitutions regarding design and construction can be made without departing from the spirit and scope of the invention.

Modifications and variations such as would be apparent to the skilled addressee are considered to fall within the scope of the present invention. The present invention is not to be limited in scope by any of the specific embodiments described herein. These embodiments are intended for the purpose of exemplification only. Functionally equivalent products, formulations and methods are clearly within the scope of the invention as described herein.

Reference to positional descriptions, such as lower and upper, are to be taken in context of the embodiments depicted in the figures, and are not to be taken as limiting the invention to the literal interpretation of the term but rather as would be understood by the skilled addressee.

Throughout this specification, unless the context requires otherwise, the word "comprise" or variations such as "comprises" or "comprising", will be understood to imply the inclusion of a stated integer or group of integers but not the exclusion of any other integer or group of integers.

The invention claimed is:

1. A vascular access device for providing prolonged vascular access for infusion of therapeutic agents and/or for insertion of one or more endovascular devices into a blood vessel, comprising:
a chamfered cannula having an inner wall defining a lumen and comprising a chamfered cannula end arranged to engage with a blood vessel at an angle and configured for connection to the blood vessel such that the lumen of the chamfered cannula at the chamfered cannula end is connected in fluid communication with and open to blood flow in the blood vessel; and
a removable plunger configured to be inserted into the lumen of the chamfered cannula and arranged to block and seal the lumen of the chamfered cannula;
wherein the removable plunger includes an outer wall that seals against the inner wall of the chamfered cannula as the removable plunger is inserted into the lumen and a chamfered end which is arranged to interface with the blood flow in the blood vessel and to eliminate dead space within the chamfered end of the chamfered cannula when the removable plunger is fully inserted in the chamfered cannula to block and seal the lumen of the chamfered cannula;
wherein the chamfered end of the removable plunger is arranged so that it does not protrude into the blood flow in the blood vessel when the removable plunger is fully inserted into the lumen of the chamfered cannula to block and seal the chamfered cannula, and
wherein the inner wall of the cannula defining the lumen is configured to interact with the outer wall of the removable plunger so that the removable plunger is guided during its passage through the lumen so that the chamfered end of the plunger is correctly aligned in the chamfered cannula and cannot rotate within the chamfered cannula.

2. The vascular access device of claim 1, wherein the chamfered cannula end and the chamfered end of the removable plunger have the same chamfered angle.

3. The vascular access device claim of 60, wherein the inner wall of the chamfered cannula defining the lumen is profiled to matingly correspond to the outer wall of the removable plunger so that the removable plunger cannot rotate due to the mating correspondence with the inner wall of the chamfered cannula.

4. The vascular access device of claim 3, wherein one or more projections of the outer wall of the removable plunger are arranged to be received in corresponding recesses in the inner wall of the chamfered cannula.

5. The vascular access device of claim 3, wherein the mating correspondence of the inner wall of the chamfered cannula and the outer wall of the removable plunger is arranged so that the chamfered cannula end is parallel with and aligned with the chamfered end of the removable plunger when the removable plunger is fully inserted in the chamfered cannula.

6. The vascular access device of claim 1, wherein the chamfered cannula end is configured as a graft end configured and arranged to engage and connect with the blood vessel via a vascular graft.

7. The vascular access device of claim 1, wherein the chamfered cannula includes a connector assembly distal to the chamfered cannula end arranged to connect to a medical supply device.

8. The vascular access device of claim 7, wherein the connector assembly is arranged to connect the medical supply device with a body portion of the chamfered cannula.

9. A vascular access device for prolonged access to a blood vessel, comprising:
a chamfered cannula having an inner wall defining a lumen for infusion of a therapeutic agent and/or for insertion of one or more endovascular devices therethrough into a blood vessel, the chamfered cannula having a chamfered end arranged to engage with a blood vessel at an angle and configured for connection to the blood vessel such that the lumen of the chamfered cannula at the chamfered end is connected in fluid communication with the blood vessel; and
a removable plunger configured to be inserted into the lumen of the chamfered cannula and arranged to block and seal the lumen of the chamfered cannula;
wherein the removable plunger has an outer wall that seals against the inner wall defining the lumen of the chamfered cannula as the removable plunger is inserted within the lumen, the removable plunger having a chamfered end which is arranged to interface with the blood flow in the blood vessel and to eliminate dead space within the chamfered end of the chamfered cannula when the removable plunger is fully inserted in the chamfered cannula to block and seal the lumen of the chamfered cannula;
wherein the chamfered end of the removable plunger is arranged so that it does not protrude into the blood flow in the blood vessel when the removable plunger is fully inserted into the lumen of the chamfered cannula to block and seal the chamfered cannula, and
wherein the inner wall defining the lumen of the chamfered cannula is profiled to matingly correspond to the outer wall of the removable plunger so that the removable plunger is guided during its passage through the lumen and cannot rotate due to the mating correspondence with the inner wall of the chamfered cannula as the removable plunger is inserted into the lumen of the chamfered cannula.

10. The vascular access device of claim 9, wherein one or more projections of the outer wall of the removable plunger are arranged to be received in corresponding recesses in the inner wall of the chamfered cannula.

11. The vascular access device of claim 9, wherein the mating correspondence of the inner wall of the chamfered cannula and the outer wall of the removable plunger is arranged so that the chamfered end of the chamfered cannula is parallel with and aligned with the chamfered end of the removable plunger when the removable plunger is fully inserted in the chamfered cannula.

12. The vascular access device of claim 9, wherein the chamfered end of the chamfered cannula is configured and arranged to engage and connect with the blood vessel via a vascular graft.

13. The vascular access device of claim 9, wherein an end of the chamfered cannula remote from the chamfered end includes a connector assembly arranged to connect to a medical supply device.

14. The vascular access device of claim 13, wherein the connector assembly is adapted to connect the medical supply device with a body portion of the chamfered cannula.

* * * * *